US012637500B2

(12) United States Patent
Torigoe et al.

(10) Patent No.: US 12,637,500 B2
(45) Date of Patent: May 26, 2026

(54) TUMOR ANTIGEN PEPTIDE

(71) Applicant: Niigata University, Niigata (JP)

(72) Inventors: Toshihiko Torigoe, Sapporo (JP);
Takayuki Kanaseki, Sapporo (JP);
Vitaly Kochin, Sapporo (JP); Yasuhiro Kikuchi, Sapporo (JP)

(73) Assignee: Niigata University, Niigata (JP)

( * ) Notice: Subject to any disclaimer, the term of this patent is extended or adjusted under 35 U.S.C. 154(b) by 590 days.

(21) Appl. No.: 16/065,488

(22) PCT Filed: Dec. 27, 2016

(86) PCT No.: PCT/JP2016/088904
§ 371 (c)(1),
(2) Date: Dec. 20, 2018

(87) PCT Pub. No.: WO2017/115798
PCT Pub. Date: Jul. 6, 2017

(65) Prior Publication Data
US 2019/0117751 A1 Apr. 25, 2019

(30) Foreign Application Priority Data

Dec. 28, 2015 (JP) .................................. 2015-257195

(51) Int. Cl.
| | |
|---|---|
| *C07K 14/705* | (2006.01) |
| *A61K 31/7088* | (2006.01) |
| *A61K 31/713* | (2006.01) |
| *A61K 35/17* | (2015.01) |
| *A61K 39/00* | (2006.01) |
| *A61K 39/39* | (2006.01) |
| *A61K 48/00* | (2006.01) |
| *A61P 35/00* | (2006.01) |
| *C07K 14/47* | (2006.01) |
| *C07K 16/28* | (2006.01) |
| *C07K 16/30* | (2006.01) |
| *C12N 5/12* | (2006.01) |
| *C12N 9/10* | (2006.01) |
| *C12N 9/12* | (2006.01) |
| *C12N 15/09* | (2006.01) |
| *C12N 15/113* | (2010.01) |
| *G01N 33/575* | (2026.01) |

(52) U.S. Cl.
CPC ........ *C07K 14/705* (2013.01); *A61K 31/7088* (2013.01); *A61K 31/713* (2013.01); *A61K 35/17* (2013.01); *A61K 39/001102* (2018.08); *A61K 39/001184* (2018.08); *A61K 39/39* (2013.01); *A61K 48/00* (2013.01); *A61P 35/00* (2018.01); *C07K 14/4702* (2013.01); *C07K 14/4748* (2013.01); *C07K 16/2833* (2013.01); *C07K 16/30* (2013.01); *C12N 5/12* (2013.01); *C12N 9/1007* (2013.01); *C12N 9/12* (2013.01); *C12N 15/09* (2013.01); *C12N 15/113* (2013.01); *C12Y 201/01043* (2013.01);
*C12Y 207/12001* (2013.01); *G01N 33/575* (2026.01); *G01N 33/5758* (2026.01); *A61K 2039/572* (2013.01); *A61K 2039/892* (2018.08)

(58) Field of Classification Search
CPC ........ A61K 39/001102; A61K 31/7088; A61K 31/713; A61K 35/17; A61K 39/001184; A61K 39/39; A61K 48/00; A61P 35/00; C07K 14/4702; C07K 14/4748; C07K 14/705; C07K 16/2833; C07K 16/30; C12N 5/12; C12N 9/1007
See application file for complete search history.

(56) References Cited

U.S. PATENT DOCUMENTS

| | | | | |
|---|---|---|---|---|
| 2007/0154915 A1* | 7/2007 | Inazawa | ............... | C12Q 1/6886 435/6.12 |
| 2008/0312096 A1* | 12/2008 | Gray | ................ | G01N 33/57449 506/9 |
| 2014/0094387 A1 | 4/2014 | Hamamoto et al. | | |
| 2016/0166666 A1 | 6/2016 | Masuda et al. | | |

FOREIGN PATENT DOCUMENTS

| | | | | |
|---|---|---|---|---|
| EP | 1 440 981 | * | 7/2004 | ............. C07K 14/47 |
| EP | 2915883 A1 | | 9/2015 | |
| JP | 2005-502329 | | 1/2005 | |
| JP | 2005-520543 A | | 7/2005 | |

(Continued)

OTHER PUBLICATIONS

Tsuji et al. (Blood, 106(2): 470-476, 2005).*

(Continued)

*Primary Examiner* — Nelson B Moseley, II
(74) *Attorney, Agent, or Firm* — Wolf, Greenfield & Sacks, P.C.

(57) ABSTRACT

The object of the present invention is to provide a detecting agent for specifically detecting a tumor cell, a tumor antigen peptide-specifically presented on a tumor cell, a pharmaceutical composition useful for the prevention and/or treatment of cancer, the pharmaceutical composition containing the tumor antigen peptide as an active ingredient, etc. The above object has been achieved by a tumor antigen peptide or its motif-substituted product, the tumor antigen peptide comprising 8 to 14 consecutive amino acids in an amino acid sequence of a protein encoded by a gene selected from the group consisting of PVT1, SUV39H2, ZNF724P, SNRNP40, and DYRK4, the tumor antigen peptide having an HLA binding ability.

10 Claims, 16 Drawing Sheets
Specification includes a Sequence Listing.

(56)          References Cited

FOREIGN PATENT DOCUMENTS

| JP | 2010-508861 | A | 3/2010 | |
| JP | 2014-523736 | | 9/2014 | |
| JP | 2015/005479 | A1 | 1/2015 | |
| WO | WO 00/55351 | * | 9/2000 | ............. C12P 21/04 |
| WO | WO 2003/000864 | A2 | 1/2003 | |
| WO | WO 2003/080808 | A2 | 10/2003 | |
| WO | WO 2004/029070 | A2 | 4/2004 | |
| WO | WO 2004/072257 | * | 8/2004 | |
| WO | WO 2008/021290 | * | 2/2008 | ............. C12Q 1/00 |
| WO | WO 2008/058944 | A1 | 5/2008 | |
| WO | WO 2009/126537 | A1 | 10/2009 | |
| WO | WO 2010/050268 | A1 | 5/2010 | |
| WO | WO 2012/164936 | * | 12/2012 | ............. C12N 15/09 |
| WO | WO 2012/164936 | A1 | 12/2012 | |
| WO | WO 2014/041185 | A2 | 3/2014 | |
| WO | WO 2014/152741 | A1 | 9/2014 | |
| WO | WO 2016/170139 | A1 | 10/2016 | |

OTHER PUBLICATIONS

Gårdsvoll et al. (Journal of Immunological Methods, 234: 107-116, 2000).*

Raschke (Current Opinion in Structural Biology, 16: 152-159, 2006).*

Murakami (The Open Biotechnology Journal, 7: 10-14, 2013).*

Asano et al., Cancer vaccine therapy with peptides targeting cancer cells. Bio Clinica. 2015. 30(3):26-30.

PCT/JP2016/088904, Apr. 11, 2017, International Search Report and English translation thereof.

* cited by examiner

[Fig. 1]
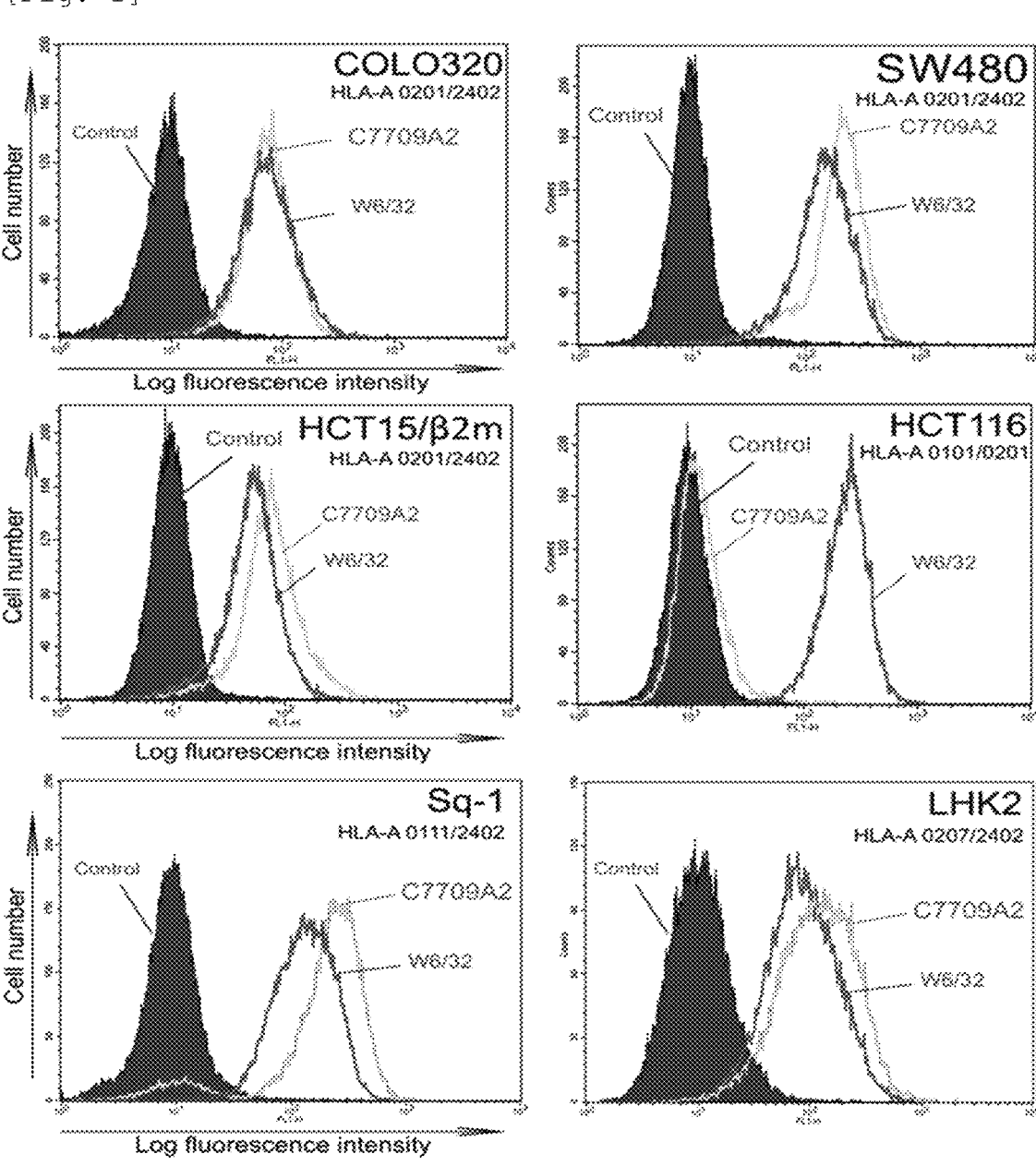

[Fig. 2-1]
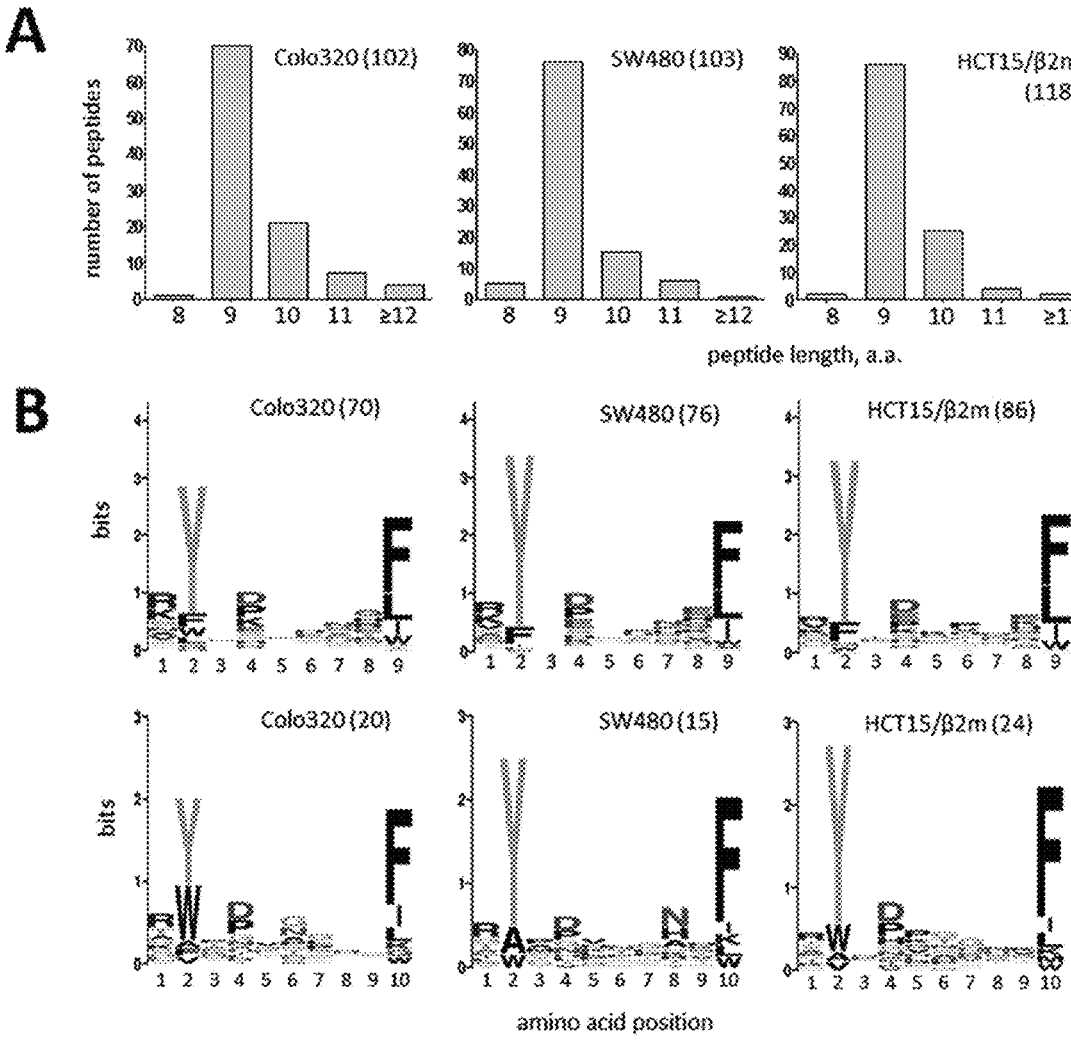

[Fig. 2-2]
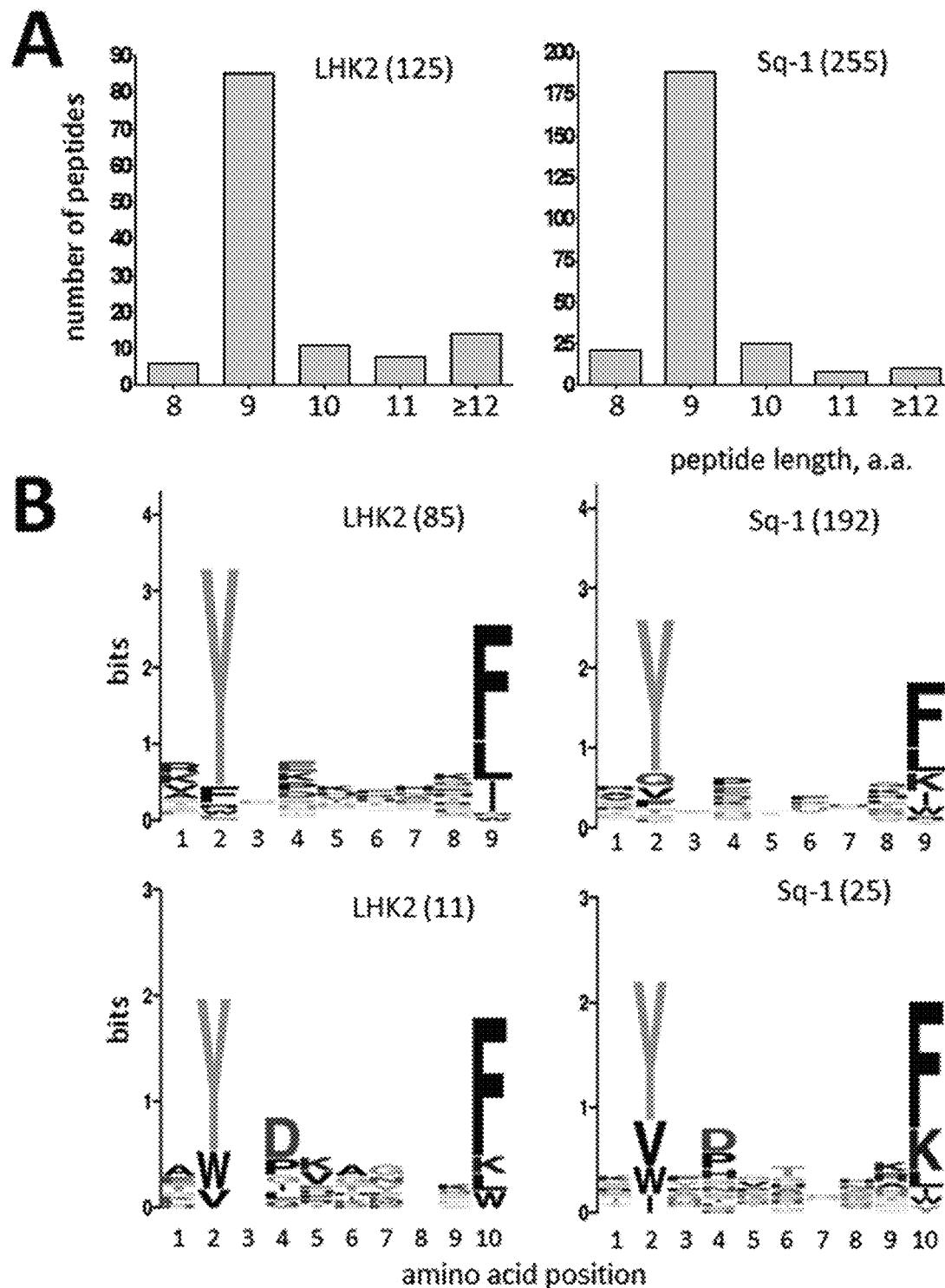

[Fig. 3]
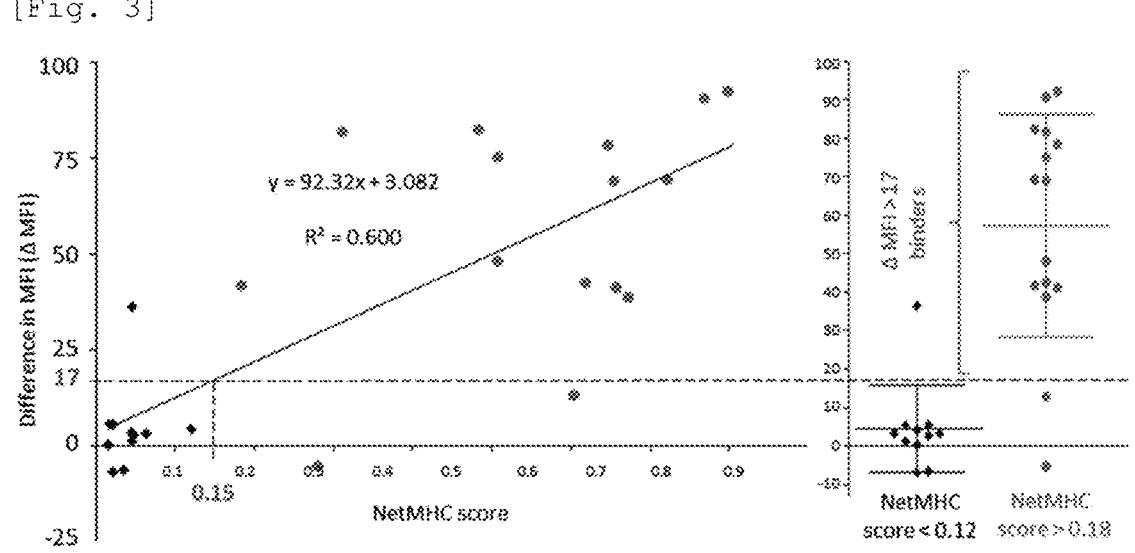

[Fig. 4-1]
A
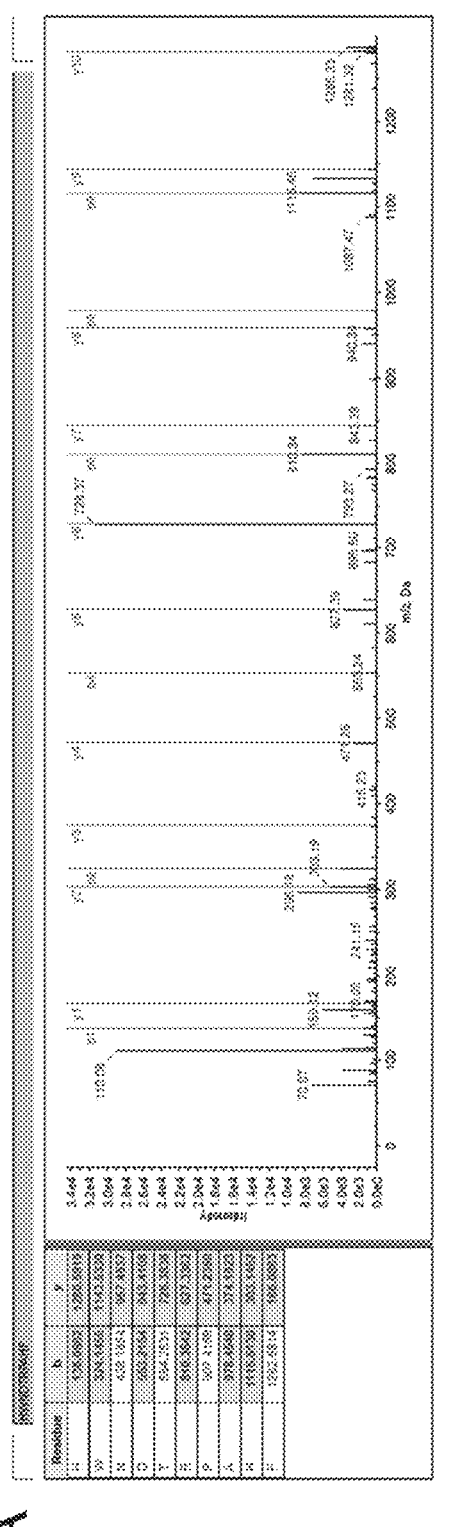
B
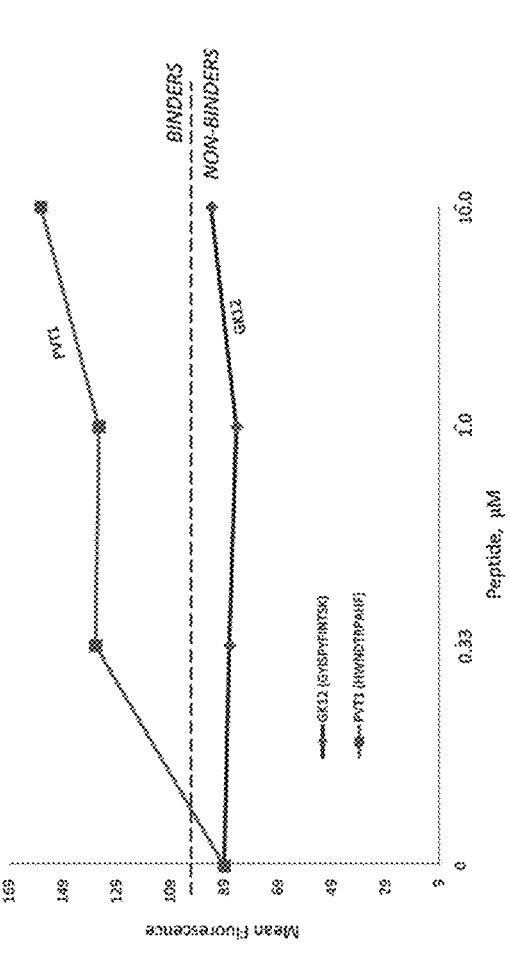

[Fig. 4-2]
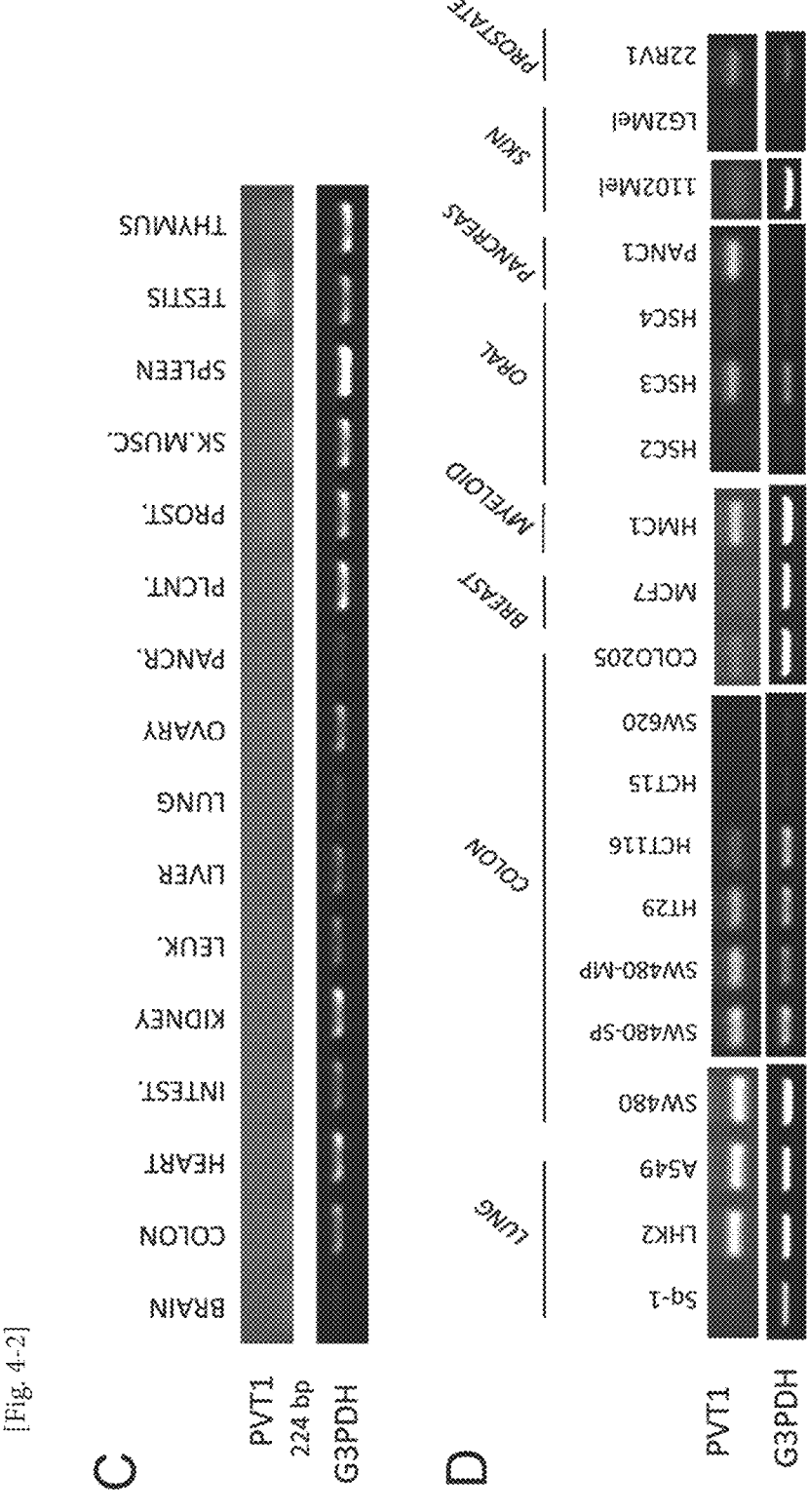

[Fig. 5-1]
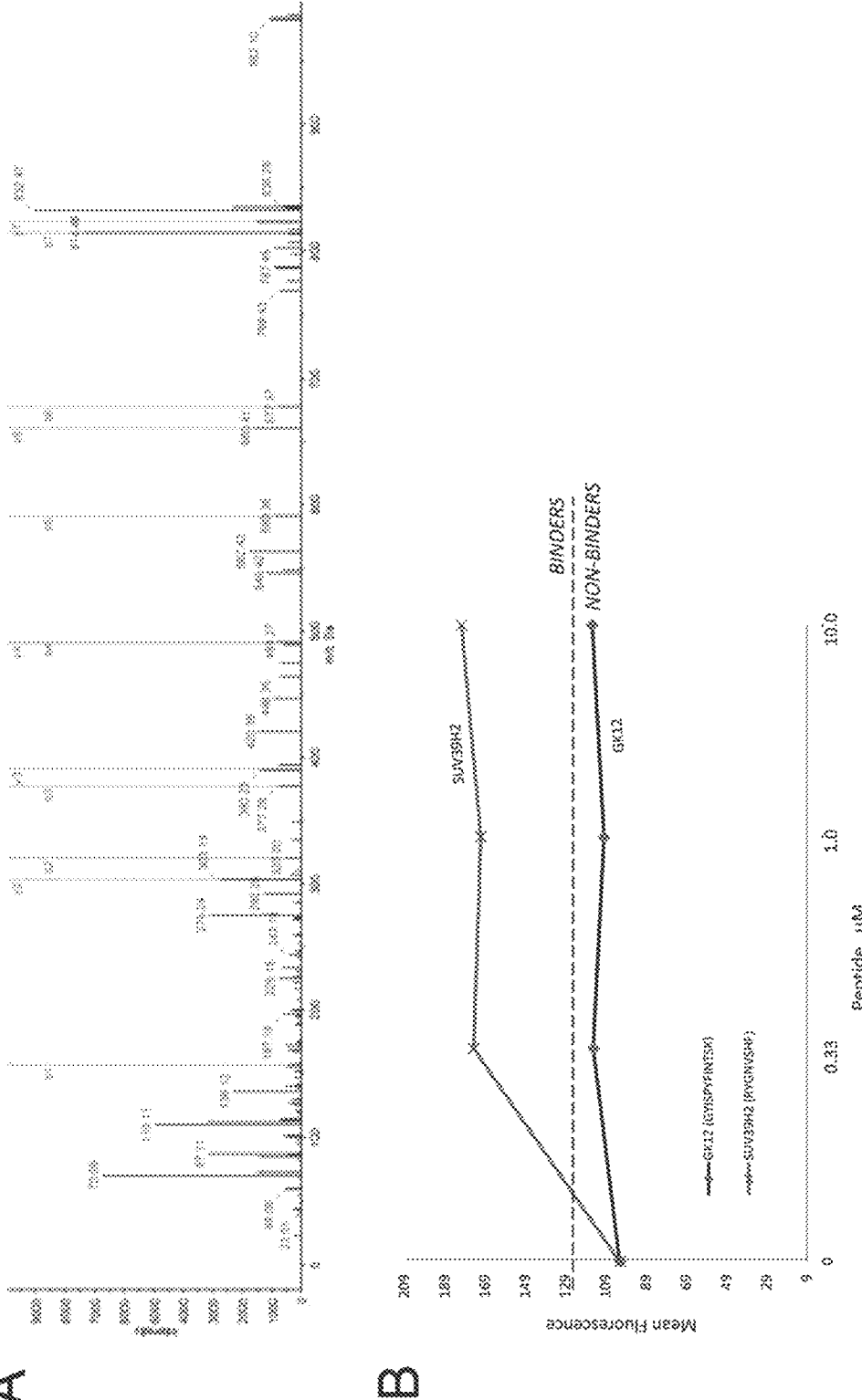

[Fig. 5-2]
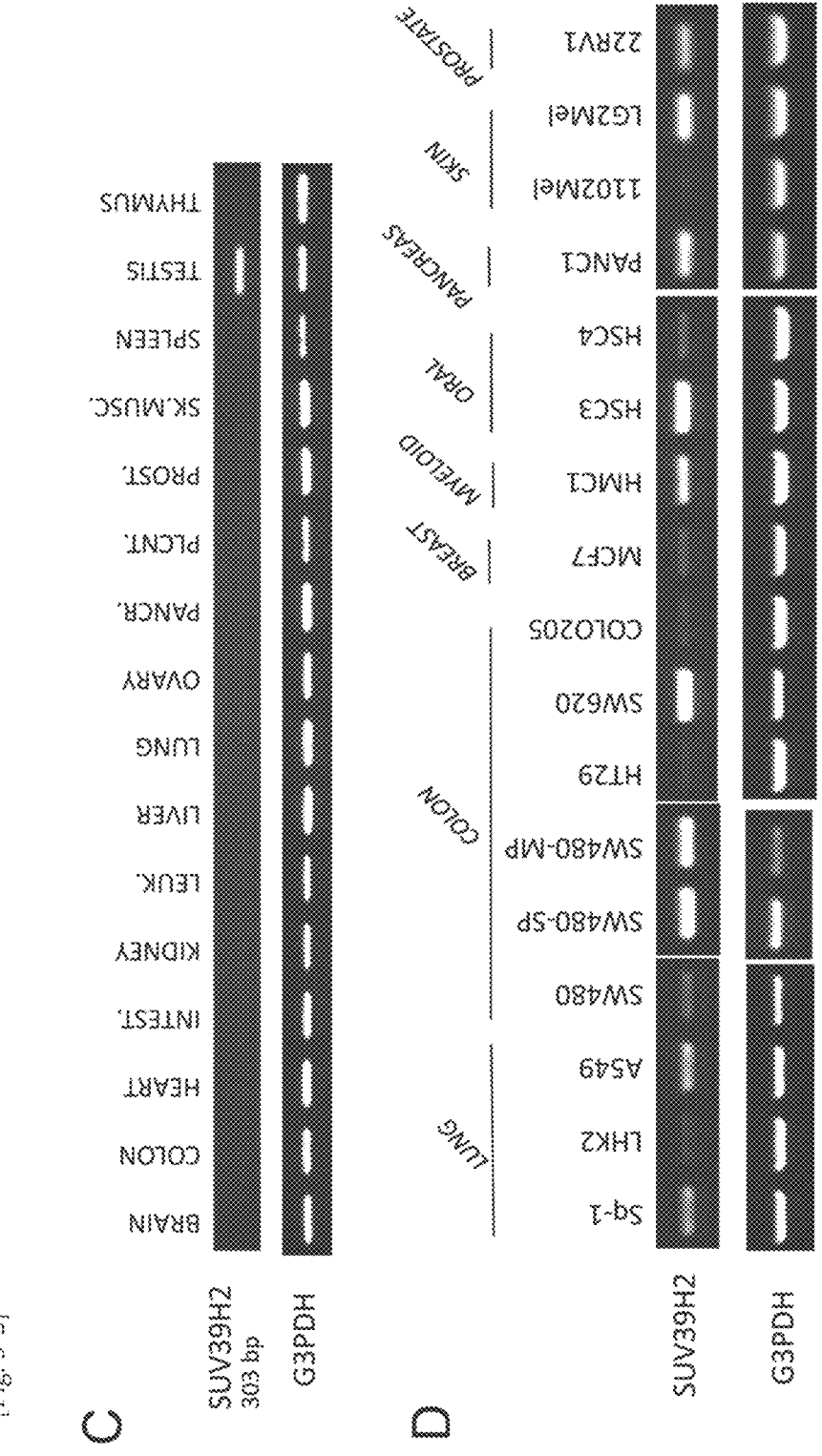

[Fig. 6-1]
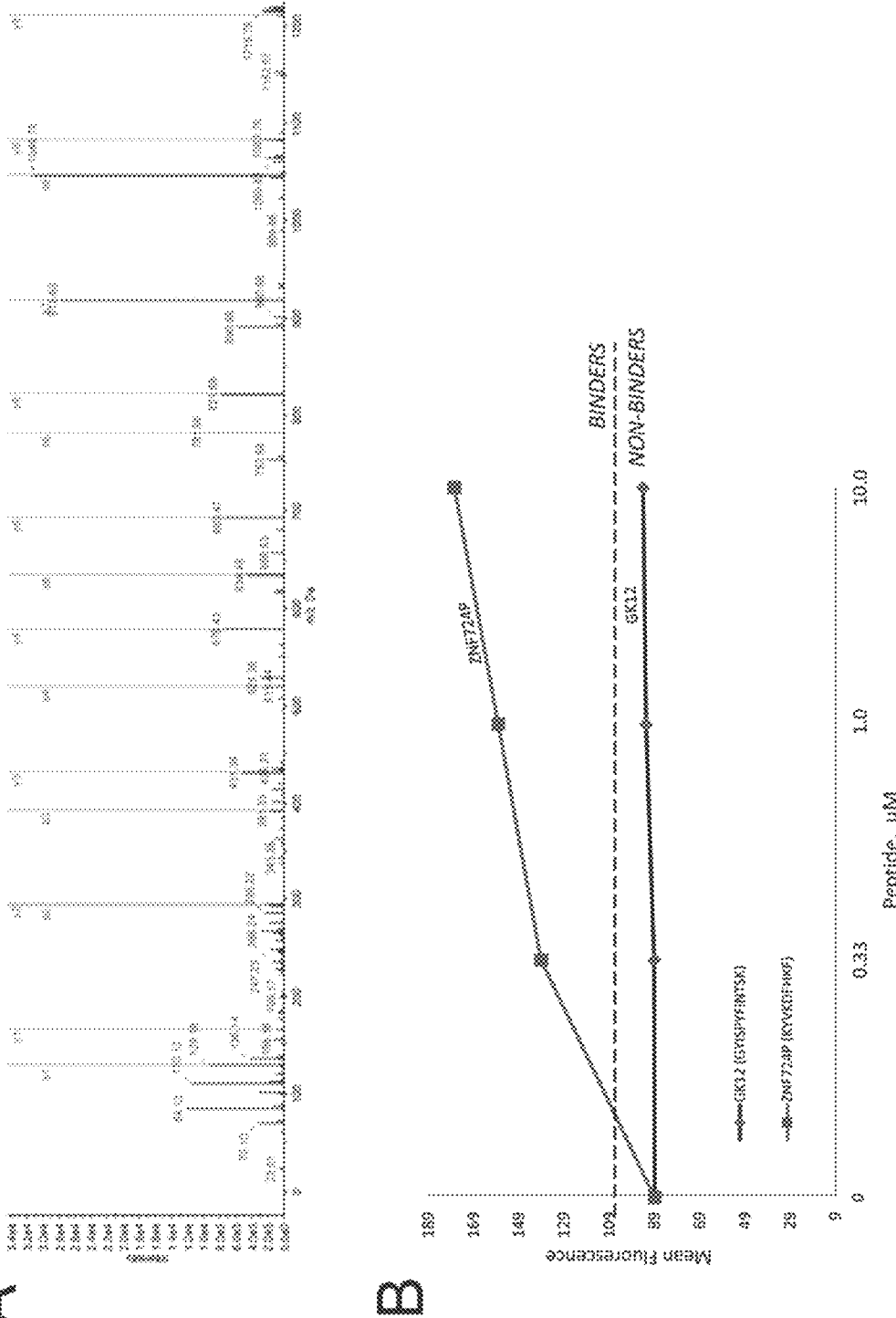

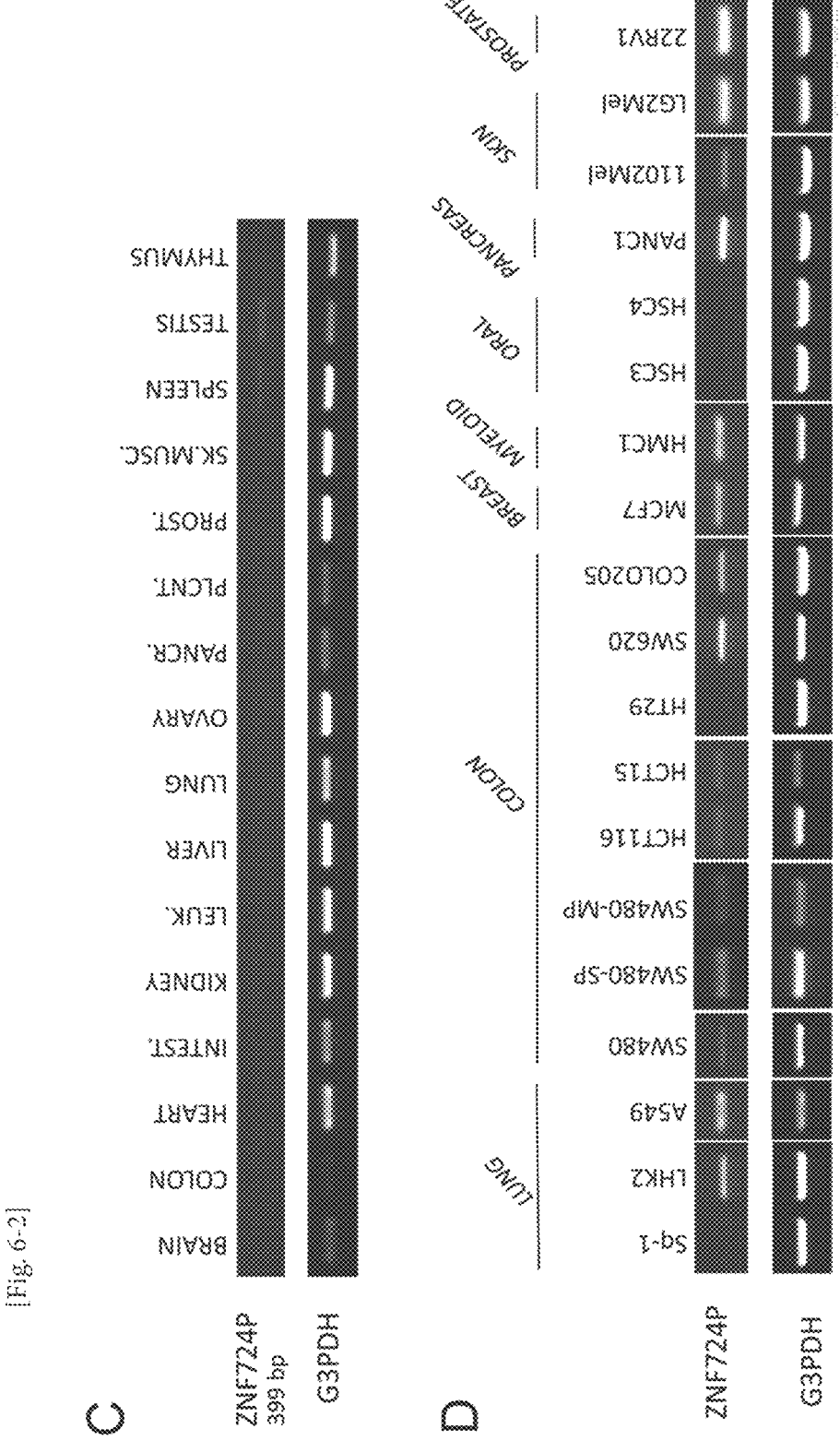
[Fig. 6-2]

[Fig. 7]
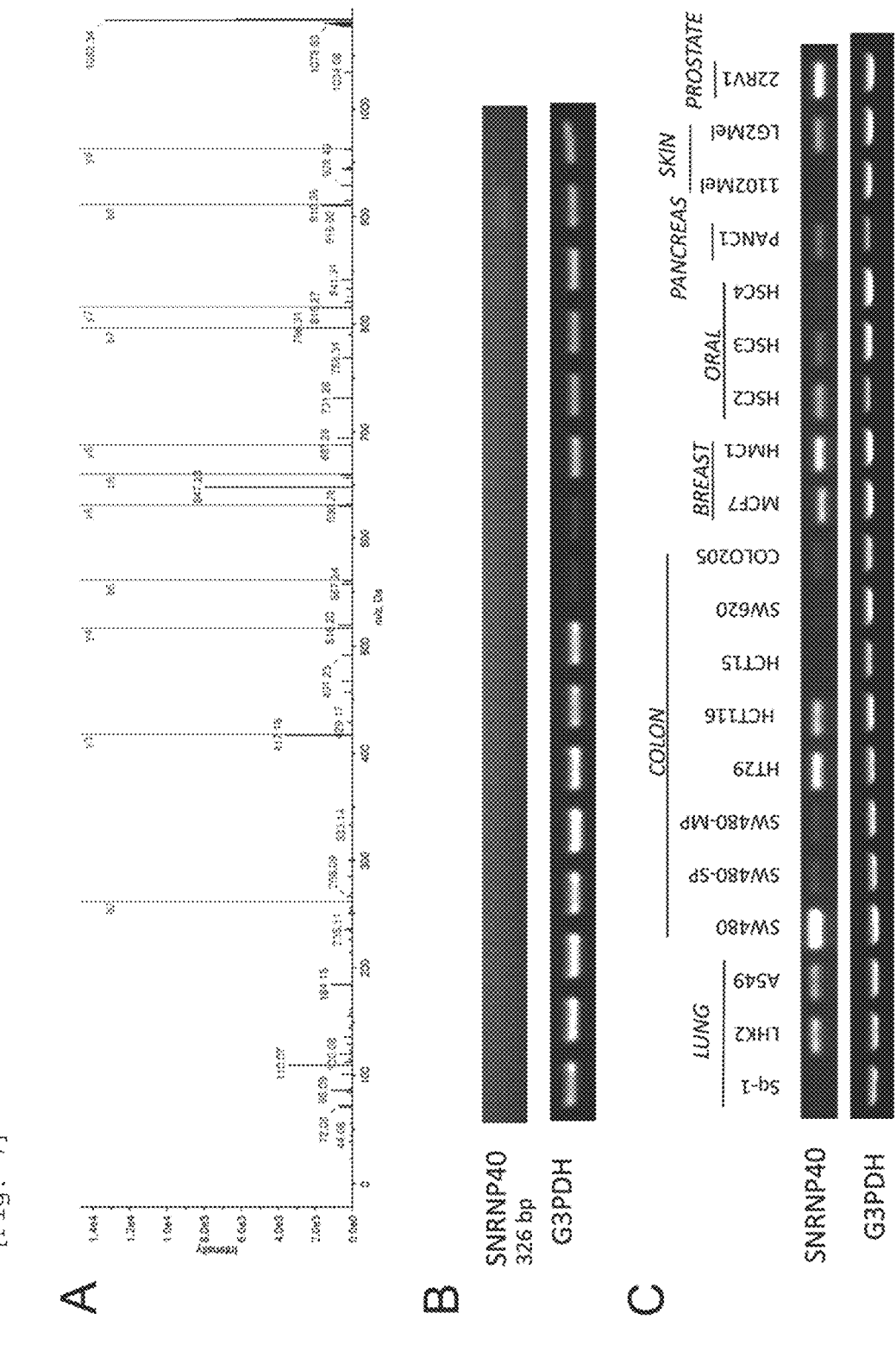

[Fig. 8-1]
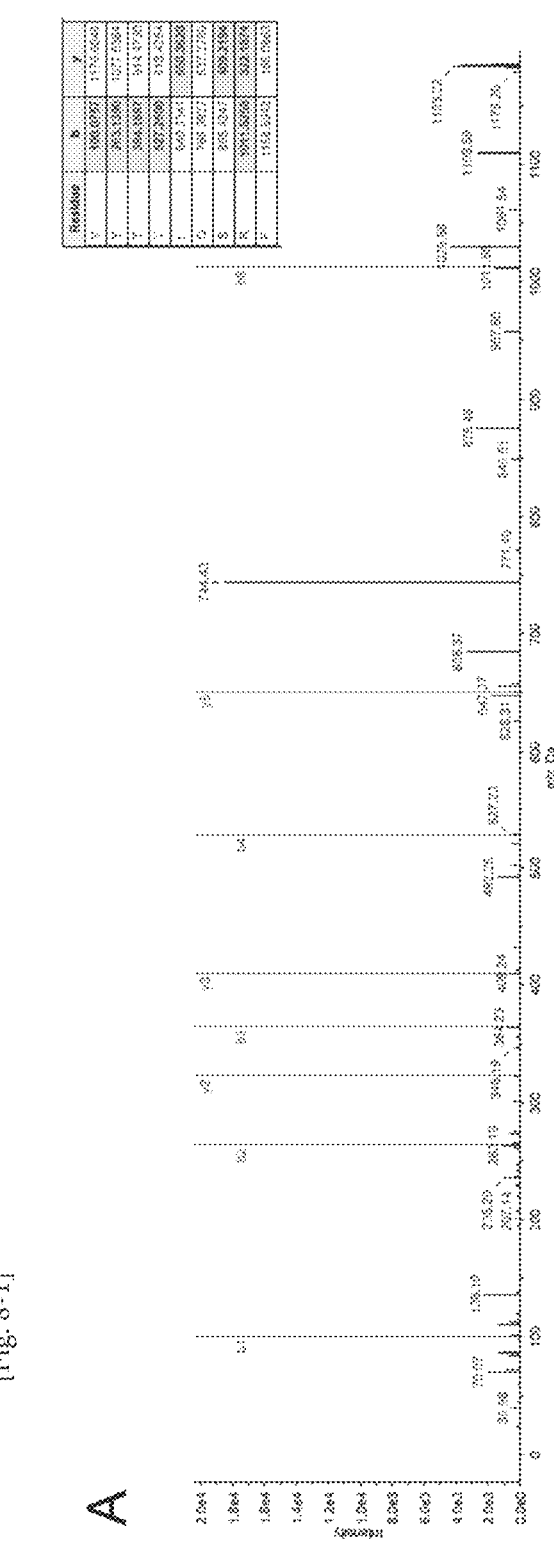

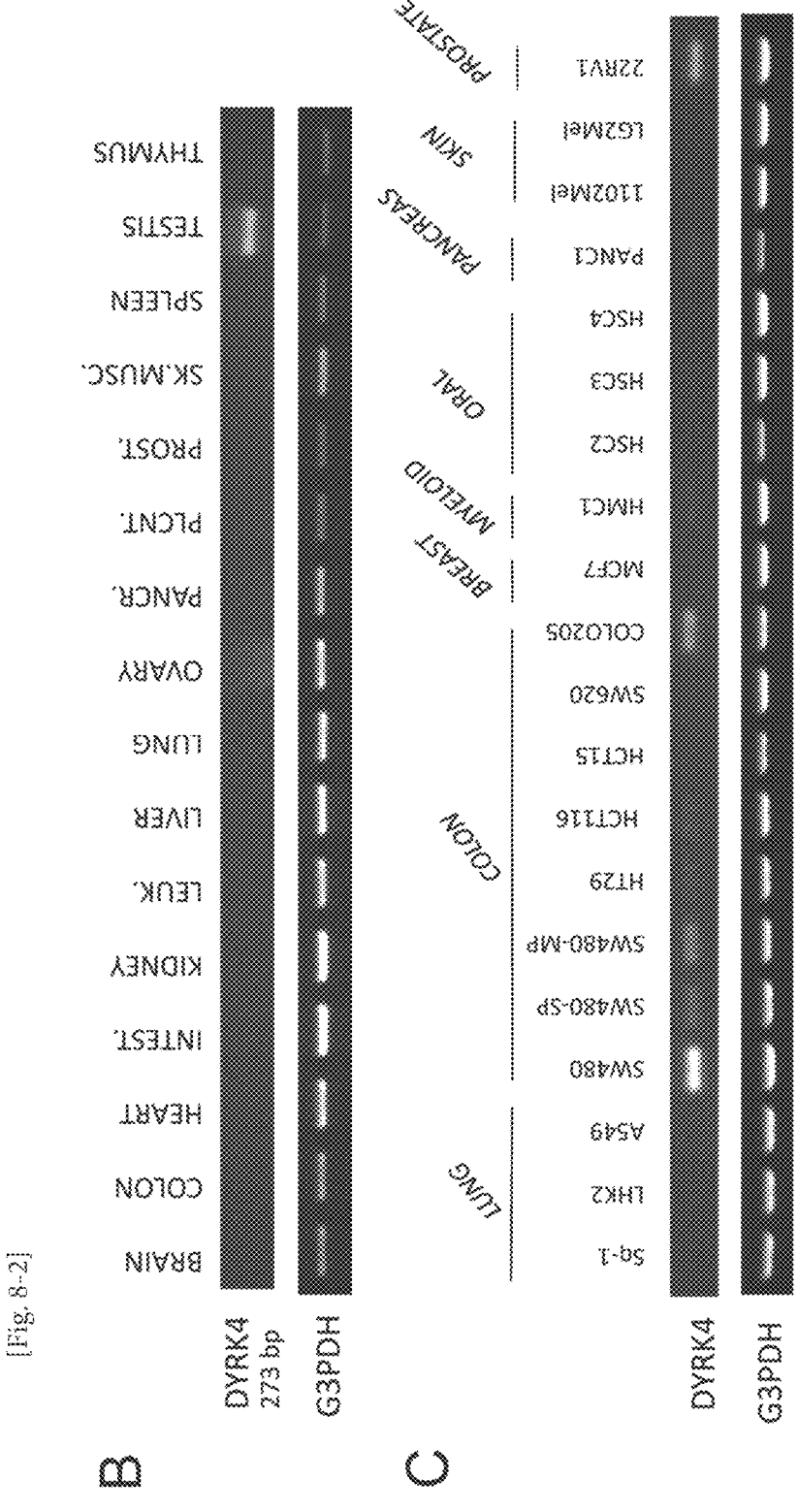
[Fig. 8-2]

[Fig. 9]
A
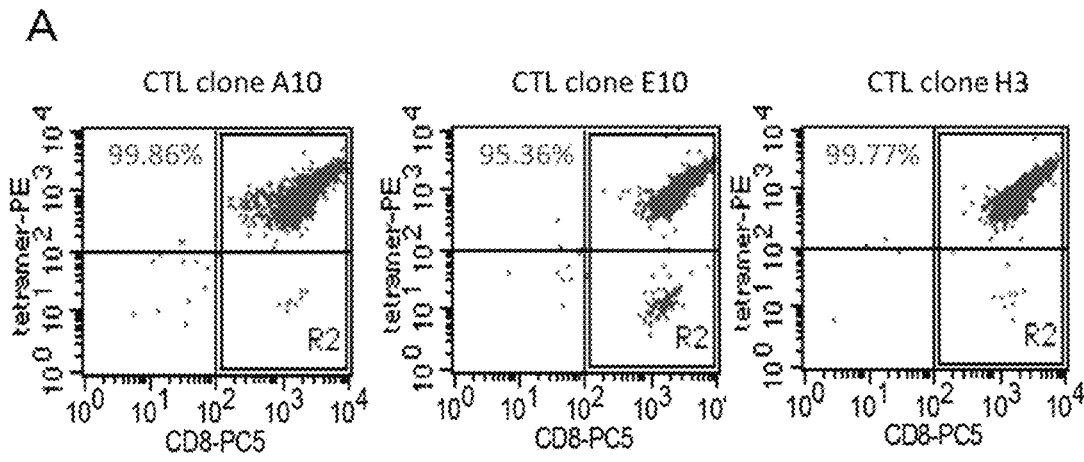
B          CTL clone 11
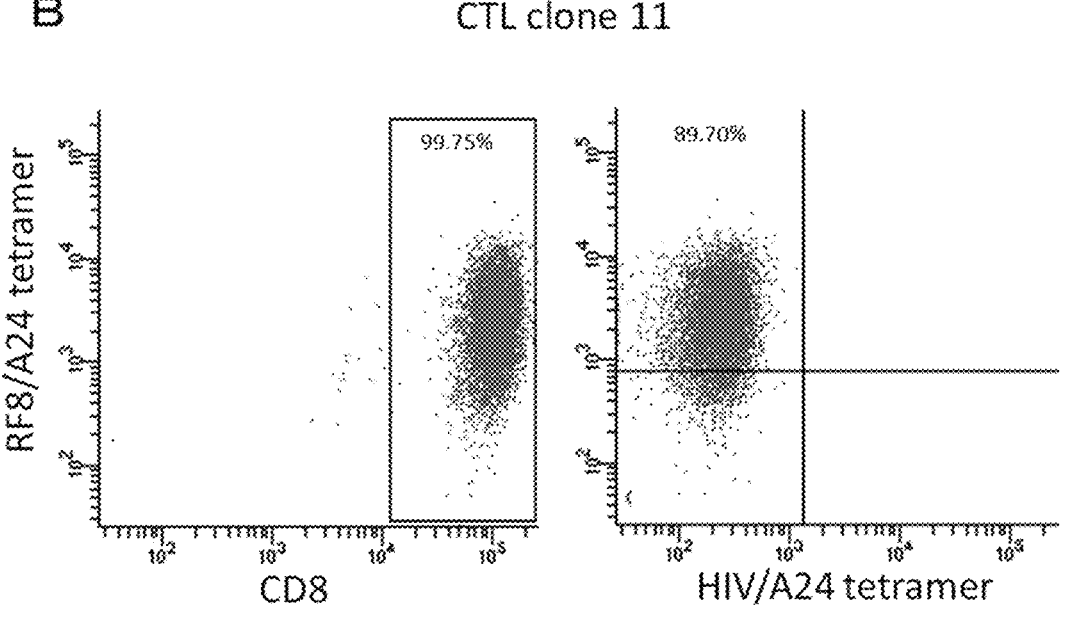

[Fig. 10-1]
A          H3     E10     A10
Peptide (−)
HIV Peptide
HF10 Peptide
SW480
colo320
Sq-1
[Fig. 10-2]
B
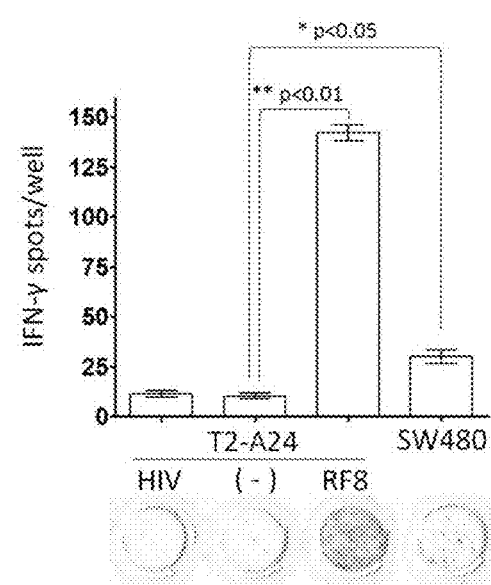

[Fig. 11]
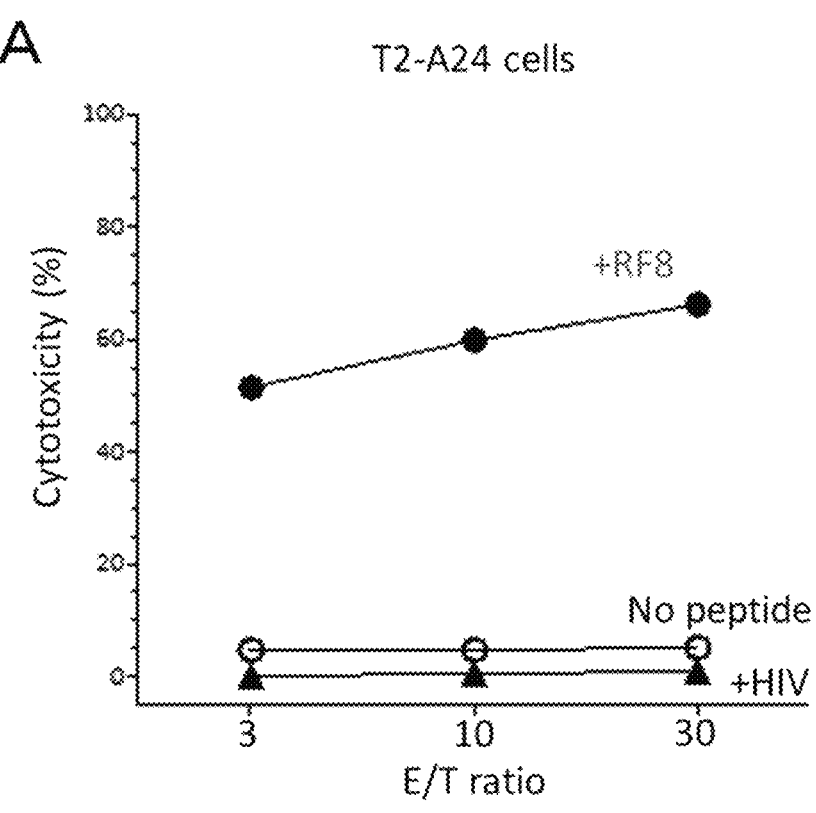
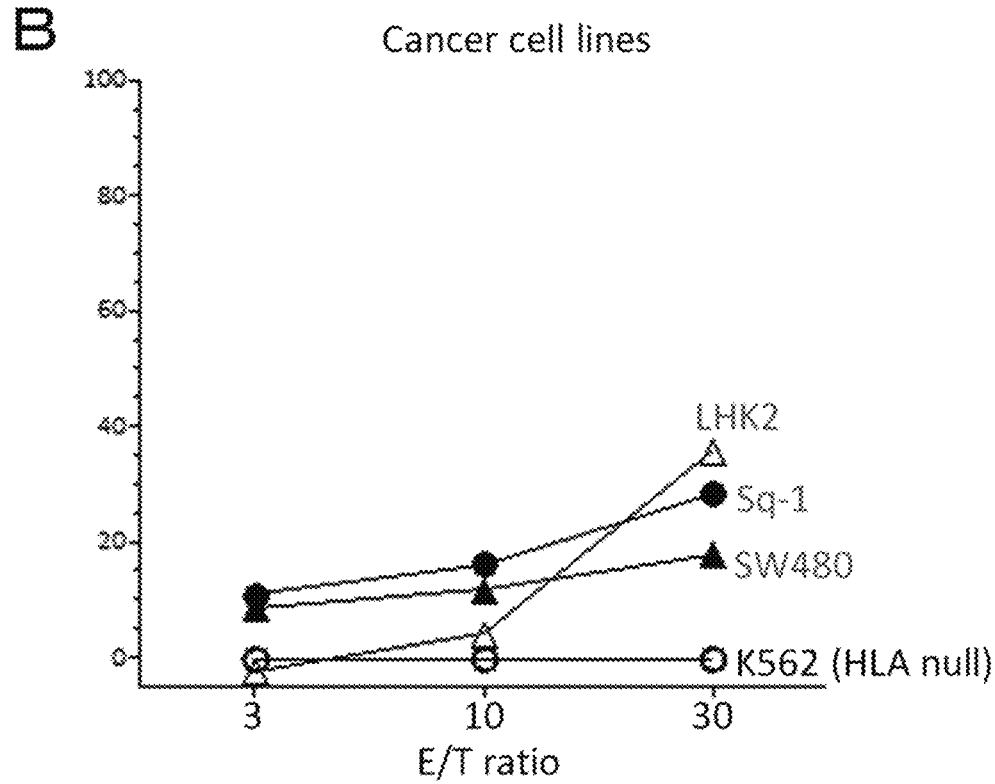

SEQUENCE LISTING

<160> NUMBER OF SEQ ID NOS: 16

<210> SEQ ID NO 1
<211> LENGTH: 10
<212> TYPE: PRT
<213> ORGANISM: Artificial
<220> FEATURE:
<223> OTHER INFORMATION: Synthetic peptide

<400> SEQUENCE: 1

His Trp Asn Asp Thr Arg Pro Ala His Phe
1                   5                   10

<210> SEQ ID NO 2
<211> LENGTH: 8
<212> TYPE: PRT
<213> ORGANISM: Artificial
<220> FEATURE:
<223> OTHER INFORMATION: Synthetic peptide

<400> SEQUENCE: 2

Arg Tyr Gly Asn Val Ser His Phe
1                   5

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Lys Tyr Val Lys Asp Phe His Lys Phe
1                   5

<210> SEQ ID NO 4
<211> LENGTH: 9
<212> TYPE: PRT
<213> ORGANISM: Artificial
<220> FEATURE:
<223> OTHER INFORMATION: Synthetic peptide

<400> SEQUENCE: 4

Ile Phe Gln Gly Asn Val His Asn Phe
1                   5

<210> SEQ ID NO 5
<211> LENGTH: 9
<212> TYPE: PRT
<213> ORGANISM: Artificial
<220> FEATURE:
<223> OTHER INFORMATION: Synthetic peptide

<400> SEQUENCE: 5

Val Tyr Thr Tyr Ile Gln Ser Arg Phe
1                   5

<210> SEQ ID NO 6
<211> LENGTH: 12
<212> TYPE: PRT
<213> ORGANISM: Artificial
<220> FEATURE:
<223> OTHER INFORMATION: synthetic peptide

<400> SEQUENCE: 6

Gly Tyr Ile Ser Pro Tyr Phe Ile Asn Thr Ser Lys
1                   5                   10

<210> SEQ ID NO 7
<211> LENGTH: 20
<212> TYPE: DNA
<213> ORGANISM: Artificial
<220> FEATURE:
<223> OTHER INFORMATION: forward primer for PVT1

<400> SEQUENCE: 7
ctgtgacctg tggagacacg                                                    20

<210> SEQ ID NO 8
<211> LENGTH: 20
<212> TYPE: DNA
<213> ORGANISM: Artificial
<220> FEATURE:
<223> OTHER INFORMATION: reverse primer for PVT1

<400> SEQUENCE: 8
cacagcctcc cttaaaacca                                                    20

<210> SEQ ID NO 9
<211> LENGTH: 20
<212> TYPE: DNA
<213> ORGANISM: Artificial
<220> FEATURE:
<223> OTHER INFORMATION: forward primer for SUV39H2

<400> SEQUENCE: 9
cgaactagca atggacgtgg                                                    20

<210> SEQ ID NO 10
<211> LENGTH: 21
<212> TYPE: DNA
<213> ORGANISM: Artificial
<220> FEATURE:
<223> OTHER INFORMATION: reverse primer for SUV39H2

<400> SEQUENCE: 10
caatgctatt cggggaagac g                                                  21

<210> SEQ ID NO 11
<211> LENGTH: 18
<212> TYPE: DNA
<213> ORGANISM: Artificial
<220> FEATURE:
<223> OTHER INFORMATION: forward primer for ZNF724P

<400> SEQUENCE: 11
ccaagacctt cggccaga                                                      18

<210> SEQ ID NO 12
<211> LENGTH: 20
<212> TYPE: DNA
<213> ORGANISM: Artificial
<220> FEATURE:
<223> OTHER INFORMATION: reverse primer for ZNF724P

<400> SEQUENCE: 12
tgagaaaggg ttgaggacac                                                    20

<210> SEQ ID NO 13
<211> LENGTH: 20
<212> TYPE: DNA
<213> ORGANISM: Artificial
<220> FEATURE:

-continued

```
<223> OTHER INFORMATION: forward primer for SNRNP40

<400> SEQUENCE: 13
ataaaaccgt ggctgtgtgg                                          20

<210> SEQ ID NO 14
<211> LENGTH: 20
<212> TYPE: DNA
<213> ORGANISM: Artificial
<220> FEATURE:
<223> OTHER INFORMATION: reverse primer for SNRNP40

<400> SEQUENCE: 14
cactgaatct gcatggcctc                                          20

<210> SEQ ID NO 15
<211> LENGTH: 20
<212> TYPE: DNA
<213> ORGANISM: Artificial
<220> FEATURE:
<223> OTHER INFORMATION: forward primer for DYRK4

<400> SEQUENCE: 15
ccaaggcaga ggagaagtca                                          20

<210> SEQ ID NO 16
<211> LENGTH: 20
<212> TYPE: DNA
<213> ORGANISM: Artificial
<220> FEATURE:
<223> OTHER INFORMATION: reverse primer for DYRK4

<400> SEQUENCE: 16
ccttcccgat tgtctccaga                                          20
```

TUMOR ANTIGEN PEPTIDE

RELATED APPLICATION

This Application is a national stage filing under 35 U.S.C. § 371 of International Patent Application Serial No. PCT/JP2016/088904, filed Dec. 27, 2016, the content of which is incorporated herein by reference in its entirety.

REFERENCE TO AN ELECTRONIC SEQUENCE LISTING

The contents of the electronic sequence listing (K044870077US00-SUBSEQ-JRV.txt; Size: 3,265 bytes; and Date of Creation: Jan. 26, 2024) is herein incorporated by reference in its entirety.

TECHNICAL FIELD

The present invention relates to a detecting agent for detecting a tumor cell by using a gene that is specifically expressed in a tumor cell, a tumor antigen peptide derived from the gene, which is useful as a preventive and/or therapeutic agent for cancer, and the use thereof.

BACKGROUND ART

Conventionally, surgical treatment (operation), radiation therapy, and chemotherapy with the use of an anticancer agent, etc. are said to be the three major therapies for cancer. However, these therapies have many problems, such as it being difficult to completely remove the focus depending on the position of the focus or the stage, or there being strong side effects. Actually, among anticancer agents that have been developed until now, there are many agents that do not have a sufficient therapeutic effect and that are associated with strong side effects.

In order to solve such defects, research into a molecularly targeted therapy in which a specific target that is specifically- or over-expressed in an abnormal cell is attacked has been actively carried out in recent years. Further advancing therefrom, an immunotherapy in which a tumor cell is attacked by activating the autoimmune system has been receiving attention. However, although immunotherapy has few side effects since one's own immunity is activated, there are only a few that have a high therapeutic effect, and further research is required.

In the elimination of tumor cells and virus-infected cells, etc. in a living body, cell-mediated immunity, in particular cytotoxic T cells (CTLs), plays an important role. For example, in the case of the elimination of tumor cells, a CTL recognizes a complex of an antigen peptide (tumor antigen peptide) and a major histocompatibility complex (MHC) class I antigen (in the case of humans, called as HLA class I antigen) on a tumor cell and attacks and destroys the tumor cell. That is, a tumor antigen peptide is produced by intracellular degradation by a protease after a tumor-specific protein, i.e., a tumor antigen protein, has been synthesized in the cell. The tumor antigen peptide thus produced binds to an MHC class I antigen (HLA class I antigen) in the endoplasmic reticulum to form a complex, which is transported to the cell surface and is presented as an antigen. A tumor-specific CTL recognizes the complex involved in this antigen presentation, and an anti-tumor effect is exhibited via cytotoxic action, lymphokine production, etc. Accompanying the elucidation of such a series of actions, therapies enhancing cancer-specific CTLs in the body of a cancer patient by utilizing a tumor antigen protein or a tumor antigen peptide as a so-called cancer immunotherapy agent (cancer vaccine) are in the process of being developed.

A tumor antigen peptide is one formed by fragmenting a protein expressed in a tumor cell and presenting it thereon. Therefore, when developing a cancer immunotherapy, it is important to search for a tumor antigen protein that is expressed in a tumor cell and, in particular, a protein that is not expressed in a normal cell but is expressed in a tumor cell.

It is known that many proteins are expressed in a tumor cell that is not observed to be expressed in normal tissue other than the testis, and they are called 'cancer testis antigens (CT antigens)'. Since the CT antigen is mainly expressed only in the testis, in immunotherapy targeting them a normal cell will not be targeted; a search is therefore underway with the CT antigens as a suitable target for cancer immunotherapy, and proteins such as SOX2, OR7C1, and DNAJB8 have been reported as cancer testis antigens. Furthermore, it has been suggested that the cancer testis antigen is particularly strongly expressed in a cancer cell having high proliferative ability, which is referred to as a cancer stem cell/cancer initiating cell (CSC/CIC).

PRIOR ART DOCUMENTS

Patent Documents

[Patent Document 1] International Patent Application WO2010/050268
[Patent Document 2] International Patent Application WO2012/164936

SUMMARY OF THE INVENTION

Problems to be Solved by the Invention

It is an object of the present invention to provide a detecting agent that specifically detects a tumor cell, a tumor antigen peptide that is specifically presented on a tumor cell, a pharmaceutical composition useful for the prevention and/or therapy of a cancer containing the above as an active ingredient, etc.

Means for Solving the Problems

While searching for a peptide that is specifically presented as an antigen on a tumor cell even if a plurality of epitope regions that are predicted to bind to an HLA exist in the sequence of a protein specifically expressed in the tumor cell, it is not easy to identify which portion of the protein actually binds to an HLA in a living body and is presented as an antigen on the cell surface. Therefore, in order to solve such problems, the present inventors have developed a method for directly identifying a peptide that is actually presented as an antigen on a tumor (natural peptide) and have identified a large number of natural peptides. It has been found that some of such peptides are peptides that are derived from a protein that is hardly expressed in normal cells of tissue other than the testis, and as a result of further intensive investigation the present invention has been accomplished.

That is, the present invention relates to the following:

[1] a tumor antigen peptide or a motif-substituted product thereof, the tumor antigen peptide comprising 8 to 14 consecutive amino acids in an amino acid sequence of a protein encoded by a gene selected from the group consisting of PVT1, SUV39H2, ZNF724P, SNRNP40, and DYRK4, and having the ability to bind to an HLA.

[2] The tumor antigen peptide or the motif-substituted product thereof according to [1], wherein the HLA is HLA-A24.

[3] The antigen peptide according to [1] or [2], wherein the peptide has tyrosine, phenylalanine, methionine, or tryptophan at the second amino acid from the N terminal, and/or leucine, isoleucine, or phenylalanine at the C terminal amino acid, or the second amino acid from the N terminal is substituted to tyrosine, phenylalanine, methionine, or tryptophan and/or the C terminal amino acid is substituted to leucine, isoleucine, or phenylalanine in said peptide.

[4] The tumor antigen peptide according to [1] to [3], wherein it is represented by SEQ ID No: 1, SEQ ID No: 2, SEQ ID No: 3, SEQ ID No: 4, or SEQ ID No: 5.

[5] A polyepitope peptide having a plurality of linked epitope peptides, comprising at least one tumor antigen peptide according to [1] to [4] as the epitope peptide.

[6] A polynucleotide encoding at least one of the tumor antigen peptide according to [1] to [4] or the polyepitope peptide according to [5].

[7] An expression vector comprising the polynucleotide according to [6].

[8] A composition for gene transfer, the composition comprising the expression vector according to [7].

[9] A method for producing an antigen-presenting cell, the method comprising contacting in vitro a cell having antigen-presenting ability with
  (A) the tumor antigen peptide according to [1] to [4] or the polyepitope peptide according to [5], or
  (B) a polynucleotide encoding at least one of the peptide and/or the polyepitope peptide of (A).

[10] An agent for inducing a cytotoxic T cell, the agent comprising any one of (a) to (e) below as an active ingredient:
  (a) the antigen peptide according to [1] to [4] or the polyepitope peptide according to [5],
  (b) the polynucleotide according to [6],
  (c) the expression vector according to [7],
  (d) a protein encoded by a gene selected from the group consisting of PVT1, SUV39H2, ZNF724P, SNRNP40, and DYRK4, a polynucleotide encoding said protein, or an expression vector containing said polynucleotide, and
  (e) an antigen-presenting cell presenting the tumor antigen peptide according to [1] to [4] as an antigen.

[11] A method for inducing a cytotoxic T cell, the method comprising contacting a peripheral blood lymphocyte with
  (A) the tumor antigen peptide according to [1] to [4] or the polyepitope peptide according to [5],
  (B) a polynucleotide encoding at least one of the peptide and/or the polyepitope peptide of (A), or
  (C) an antigen-presenting cell presenting the tumor antigen peptide according to [1] to [4] as an antigen.

[12] A pharmaceutical composition comprising any one of (a) to (e) below as an active ingredient:
  (a) the antigen peptide according to [1] to [4] or the polyepitope peptide according to [5],
  (b) the polynucleotide according to [6],
  (c) the expression vector according to [7],
  (d) a protein encoded by a gene selected from the group consisting of PVT1, SUV39H2, ZNF724P, SNRNP40, and DYRK4, a polynucleotide encoding said protein, or an expression vector containing said polynucleotide, and
  (e) a cytotoxic T cell that specifically damages an antigen-presenting cell presenting the tumor antigen peptide according to [1] to [4] as an antigen.

[13] The pharmaceutical composition according to [12], comprising the antigen peptide according to [1] to [4] and/or the polyepitope peptide according to [5] as an active ingredient.

[14] The pharmaceutical composition according to [12] or [13] further comprising an adjuvant.

[15] The pharmaceutical composition according to [12] to [14], which is a preventive and/or therapeutic agent for a cancer.

[16] The pharmaceutical composition according to [12] to [15], which is a vaccine for prevention and/or therapy of a cancer.

[17] The pharmaceutical composition according to [12] to [16], which is used with an immune checkpoint inhibitor.

[18] An HLA multimer comprising an HLA and the antigen peptide according to [1] to [4].

[19] A diagnostic agent comprising the HLA multimer according to [18].

[20] A T cell receptor-like antibody that recognizes a complex of an HLA and the antigen peptide according to [1] to [4].

[21] A tumor detecting agent comprising the T cell receptor-like antibody according to [20].

[22] A chimeric antigen receptor that recognizes a complex of an HLA and the antigen peptide according to [1] to [4].

[23] An artificial CTL comprising a T cell receptor that recognizes a complex of an HLA and the antigen peptide according to [1] to [4].

[24] A bispecific antibody that specifically recognizes a lymphocyte surface antigen and a complex of an HLA and the antigen peptide according to [1] to [4].

[25] A tumor cell-detecting agent comprising a detecting agent for detecting an expression product of a gene selected from the group consisting of PVT1, SUV39H2, ZNF724P, SNRNP40, and DYRK4.

[26] The tumor cell-detecting agent according to [25], wherein it detects a tumor cell in a cell population comprising cells derived from one or more biological samples selected from the group consisting of lung, large intestine, small intestine, brain, heart, placenta, liver, skeletal muscle, kidney, pancreas, spleen, thymus, prostate, ovary, and blood.

[27] The tumor cell-detecting agent according to [25] or [26], wherein the gene expression product is an mRNA and/or an endogenous polypeptide.

[28] The tumor cell-detecting agent according to [25] to [27], wherein the gene expression product is an mRNA, and the tumor cell-detecting agent comprises a probe and/or primer that has a base sequence complementary to said gene.

[29] The tumor cell-detecting agent according to [25] to [28], wherein the gene expression product is an endogenous polypeptide, and the tumor cell-detecting agent comprises a detecting substance that specifically reacts with said endogenous polypeptide.

[30] The tumor cell-detecting agent according to [29], wherein the detecting substance is an antibody.

[31] A diagnostic agent for selecting a patient that is the subject of therapy for whom a method for treating cancer using the pharmaceutical composition according to [12] to [17] is effective, the diagnostic agent comprising the HLA multimer according to [18], the T cell receptor-like antibody according to [20], and/or the tumor cell-detecting agent according to [25] to [30].

[32] An antisense oligonucleotide for a gene selected from the group consisting of PVT1, SUV39H2, ZNF724P, SNRNP40, and DYRK4.

[33] An siRNA comprising an antisense region that is complementary to a gene selected from the group consisting of PVT1, SUV39H2, ZNF724P, SNRNP40, and DYRK4 and a sense region that is at least partially complementary to said antisense region.

[34] A pharmaceutical composition comprising the antisense oligonucleotide according to [32] and/or the siRNA according to [33], and pharmaceutically acceptable carrier.

[35] The pharmaceutical composition according to [34], which is a preventive and/or therapeutic agent for a cancer.

Effects of the Invention

In accordance with the present invention, a tumor antigen peptide that is useful as an inducer for a CTL that specifically attacks a tumor cell, and a pharmaceutical composition, etc., comprising the above as an active ingredient, which is useful for the prevention and/or therapy of a cancer are provided.

BRIEF DESCRIPTION OF DRAWINGS

FIG. 1 shows localization of HLA-A24 molecules in cancer cell lines SW480, HCT-116, HCT-15/β2m, Colo320, LHK2, and Sq-1. It can be seen that in the cell lines other than HCT-116, more HLA-A24 molecules are present on the cell surface than the control. This result suggests that these cells are presenting as an antigen many natural peptides that form a complex with an HLA-A24 molecule.

FIG. 2 shows the distribution of natural peptides presented as an antigen on the cell surface in each cell line. FIG. 2-1 shows large intestine cancer cell lines and FIG. 2-2 shows lung cancer cell lines; in both figures, A shows the abundance for each amino acid length of the natural peptides, and B shows the abundance ratio of amino acids at each amino acid position in peptides having a length of 9 amino acids and a length of 10 amino acids.

FIG. 3 is a graph showing the correlation between NetMHC score and AMFI studied from the result of a binding assay of 26 randomly selected natural peptides. The ordinate represents AMFI and the abscissa represents NetMHC score. In groups where the NetMHC score is less than 0.12, all of the members except one show AMFI less than 10, and in groups where the NetMHC score is larger than 0.18, all of the members except two show AMFI about 40 or greater. From this result it is surmised that when the NetMHC score of a given peptide is larger than 0.15 (AMFI is larger than 17), said peptide is an HLA-A24 binding peptide.

FIG. 4 shows the result of evaluation of PVT1 and a PVT1-derived natural peptide (SEQ ID No: 1). A shows the result of MS/MS of the natural peptide. B shows the result of a binding assay of the natural peptide. C shows the expression of PVT1 in normal tissue. D shows the expression of PVT1 in various types of cancer cells.

FIG. 5 shows the result of evaluation of SUV39H2 and an SUV39H2-derived natural peptide (SEQ ID No: 2). A shows the result of MS/MS of the natural peptide. B shows the result of a binding assay of the natural peptide. C shows the expression of SUV39H2 in normal tissue. D shows the expression of SUV39H2 in various types of cancer cells.

FIG. 6 shows the result of evaluation of ZNF724P and a ZNF724P-derived natural peptide (SEQ ID No: 3). A shows the result of MS/MS of the natural peptide. 3 shows the result of a binding assay of the natural peptide. C shows the expression of ZNF724P in normal tissue. D shows the expression of ZNF724P in various types of cancer cells.

FIG. 7 shows the result of evaluation of SNRNP40 and an SNRNP40-derived natural peptide (SEQ ID No: 4). A shows the result of MS/MS of the natural peptide. B shows the expression of SNRNP40 in normal tissue. C shows the expression of SNRNP40 in various types of cancer cells.

FIG. 8 shows the result of evaluation of DYRK4 and a DYRK4-derived natural peptide (SEQ ID No: 5). A shows the result of MS/MS of the natural peptide. B shows the expression of DYRK4 in normal tissue. C shows the expression of DYRK4 in various types of cancer cells.

FIG. 9 is a dot plot showing the result of analysis of the properties of each CTL clone using an HLA-A24 tetramer reagent. In all figures the ordinate represents the fluorescence intensity of a natural antigen peptide/HLA-A24 tetramer reagent, and the abscissa represents the fluorescence intensity of CD8 in A and the left-hand figure of B and of HIV/HLA-A24 tetramer reagent in the right-hand figure of B. A used HF10 as a natural antigen peptide, and B used RF8 as a natural antigen peptide. A plurality of CTL clones were induced by the method described in Example 5 (1) of the present application when any of the natural antigen peptides was used, A represents clone A10, E10, and H3 induced by HF10, and B represents the result of clone 11 induced by RF8.

FIG. 10 shows the result of an ELISPOT assay. A represents the ELISPOT assay results using HF10 as a natural antigen peptide; the six lines on the left side show the results when clone H3 was used as a CTL, the six lines in the middle for E10, and the six lines on the right side for clone A10. B shows the ELISPOT assay results using RF8 as a natural antigen peptide and clone 11 as a CTL, and in the graph the ordinate represents the number of spots per well which IFN-γ was detected, and the abscissa represents the target cell. Furthermore, the photograph beneath the graph shows the actual spots obtained by the ELISPOT assay for each cell.

FIG. 11 is a graph showing the result of an LDH killing assay using clone 11. A shows the result when T2-A24 cells pulsed with each peptide were used as target cells, and B shows the result when various types of cancer cell lines were used as target cells.

MODES FOR CARRYING OUT THE INVENTION

The present invention is explained in detail below.

The 'epitope peptide' referred to in the present invention means a peptide that binds to an MHC (an HLA for humans), is presented as an antigen on the cell surface, and has antigenicity (can be recognized by a T cell). The epitope peptide includes a CTL epitope peptide that binds to an MHC class I, is presented as an antigen, and is recognized by a CD8-positive T cell, and a helper epitope peptide that binds to an MHC class II, is presented as an antigen, and is recognized by a CD4-positive T cell.

Among epitope peptides, a protein-derived peptide that is specifically- or over-expressed a tumor cell is in particular called a tumor antigen peptide. Antigen presentation refers to a phenomenon in which a peptide present within a cell binds to an MHC and this MHC/antigen peptide complex is localized on the cell surface. As described above, it is known that an antigen presented on a cell surface is recognized by a T cell, etc. and then activates cell-mediated immunity or humoral immunity; since an antigen presented by an MHC class I activates cell-mediated immunity and is also recognized by a T cell receptor of a naive T cell to thus induce the naive T cell to become a CTL having cytotoxic activity, a tumor antigen peptide used in immunotherapy is preferably a peptide that binds to an MHC class I and is presented as an antigen.

It is known that many peptides that bind to an MHC have a certain feature. In the present invention, this feature is called a 'binding motif'. In the present technical field, it is known which MHC binds to a peptide having which binding motif. For example, in the binding motif of HLA-A24, which is one type of human MHC, the second from the N terminal is tyrosine, phenylalanine, methionine, or tryptophan, and the amino acid at the C terminal is leucine, isoleucine, or phenylalanine.

In the present specification a 'motif-substituted product' means, for a peptide having a certain binding motif, one in which another binding motif has been substituted for said certain binding motif. A person skilled in the art will naturally understand that in the present invention the motif-substituted product exhibits equivalent effects to the peptide prior to the substitution.

In the present invention, a 'tumor' includes a benign tumor and a malignant tumor (cancer, malignant neoplasm). A cancer includes a hematopoietic tumor, an epithelial malignant tumor (carcinoma), and a nonepithelial malignant tumor (sarcoma).

In the present invention, a natural peptide of the present invention has been isolated/identified using a method described in Examples below, etc. for enabling isolation/identification of a natural peptide that is actually presented as an antigen on a cell surface. In the present invention, a 'natural peptide' means a peptide that is actually presented as an antigen on a cell surface. Furthermore, a 'natural antigen peptide' is a natural peptide that has been confirmed to have antigenicity. By isolating this natural antigen peptide from a cancer cell and determining the sequence and the origin thereof, it is possible to obtain useful findings for the targeted therapy of a cancer using CTLs.

The method of isolating/identifying natural peptides used in the present invention comprises a step of lysing a cancer stem cell presenting a natural peptide and isolating a complex of an MHC and the natural peptide from the lysate, a step of separating the isolated complex into the MHC molecule and the natural peptide to isolate the natural peptide, and a step of identifying the isolated natural peptide.

In the Examples below, for the isolation of a complex of an MHC and a natural peptide, a method of extracting the peptide/MHC complex by immunoprecipitation using a specific antibody against the MHC was adopted, but any method may be used as long as it can isolate a complex between an MHC and a natural peptide from a lysate.

In the Examples below, as suitable anti-MHC antibodies, antibodies against an HLA class I, such as anti-HLA-A24 antibody were used, but any antibody may be used as long as it can specifically recognize a complex between an MHC and a natural peptide.

In the Examples below, in the step of separating a complex into an MHC molecule and a natural peptide, peptide isolation using a weak acid was performed, but any method may be used as long as it can separate an MHC from a natural peptide.

Furthermore, in the Examples below, the sequence of the above isolated natural peptide was analyzed using a peptide sequence analysis method that combines liquid chromatography and tandem mass spectrometry, and the natural peptide that is actually presented as an antigen on the cell surface was identified, but identification may be carried out by any method as long as it can identify the sequence of a peptide.

The present inventors have analyzed natural antigen peptides that are presented as antigens on a human cancer cell. As a result, 383 peptides have been identified as natural peptides that are presented as antigens on a cancer cell. Then, expression in normal tissue of 273 genes derived from the peptides that have been found to have high HLA-A24 binding among the 383 peptides was examined, it was found that 5 genes, that is, PVT1, SUV39H2, ZNF724P, SNRNP40, and DYRK4, are so-called cancer testis antigens, which are expressed only in the testis for normal tissue.

PVT1 (Plasmacytoma variant translocation 1) is a non-coding RNA that is located on the same chromosome as is MYC which is known as a proto-oncogene, and is thought to function as an MYC activator. Furthermore, it has been reported that in a large number of cancers for which an increase in the number of MYC copies is observed, the number of PVT1 copies is similarly increased, and it has been suggested that an increase in the amount of transcribed PVT1 gene is involved in cell proliferation and malignant transformation. However, while as described above PVT1 was thought to be a non-coding RNA, the present inventors have found for the first time that a partial peptide of a protein that is predicted to be encoded by PVT1 is presented as an antigen on a cancer cell, and this surprisingly suggests the possibility that PVT1 is expressed as a protein at least in a cancer cell.

SUV39H2 (Suppressor of homolog 2 variegation 3-9 homolog 2 (Drosophila)) is a gene encoding a histone-lysine N-methyl transferase, which is a transferase that specifically trimethylates Lys-9 of histone H3. It is thought that epigenetic suppression of transcription is caused by trimethylation of histone H3, and it has been reported that the SUV39H2 protein in particular is involved in epigenetic control of the telomere length in mammalian cells. Furthermore, it has been reported that it is highly expressed in cancer cells of lung cancer, hepatocellular cancer, prostate cancer, etc. Moreover, it has been reported that it is expressed in early undifferentiated human embryonic stem cells, expression is gradually suppressed as differentiation progresses, and the expression subsequently recovers to the same level as in undifferentiated cells. Furthermore, it has been reported that when SUV39H2 is overexpressed in cancer cells the colony-forming activity of the cancer cells increases, and when SUV39H2 is knocked down in cancer cells overexpressing SUV39H2 the proliferation of cells is suppressed (Patent Document 2).

ZNF724P (zinc finger protein 724, pseudogene) is presumed to be a gene encoding one type of zinc finger protein, but there has been no report on the function of the ZNF724P protein. When considering its structural features, since it is a classical C2H2 type zinc finger protein having KRAB, its involvement in transcription control due to interaction with DNA is surmised. Furthermore, there has been no report of its involvement in tumorigenesis or stemness.

SNRNP40 small nuclear ribonucleoprotein 40 kDa (U5 protein) is a gene encoding, among small nuclear ribonucleoproteins (snRNPs) forming the spliceosome, a protein forming U5 snRNP. Therefore, the SNRNP40 protein is surmised to be involved in splicing of mRNA. There has been no report of its involvement in tumorigenesis or stemness.

DYRK4 (Dual specificity tyrosine-phosphorylation-regulated kinase 4) is a gene encoding one type of serine/threonine protein kinase. It is thought that the bispecific kinase family to which DYRK4 belongs functions in cell differentiation and proliferation control, survival, and development. It is known that DYRK4 has a plurality of isoforms including a plurality of splicing variants.

Furthermore, there has been no report of its involvement in tumorigenesis or stemness.

<1> Gene Expression Product of the Present Invention

In the present invention, when a gene name such as for example 'PVT1' is simply stated, it means, unless otherwise specified, a gene having a known nucleic acid sequence that is denoted by said gene name, and it typically means a cDNA or mRNA sequence, but it is not limited thereto as long as a person skilled in the art can recognize it as a sequence of said gene. Preferred examples of the gene and nucleic acid sequence thereof in the present invention include genes denoted by the sequences listed below.

PVT1: GenBank Accession No. NR_003367

SUV39H2: GenBank Accession Nos. NM_001193424.1 and NM_001193425

ZNF724P: GenBank Accession No. NR_045525.1

SNRNP40: GenBank Accession No. NM_004814.2

DYRK4: GenBank Accession Nos. NM_001282285.1, NM_001282286.1, NM_003845.2, and NR_104115.1

Therefore, mRNA as a gene expression product of the present invention is sometimes represented simply by the name of the gene.

In the present invention, when the notation 'protein' is added to the name of a gene, such as in 'PVT1 protein', etc., it means a protein encoded by the gene, an isoform thereof, and a homolog thereof. Examples of the isoform include a splicing variant and a variant such as an SNP based on individual difference. Specific examples include (1) a protein with an amino acid sequence that has a homology of at least 90%, preferably at least 95%, and more preferably at least 98% with a protein encoded by the gene, and (2) a protein with an amino acid sequence for which one or more amino acids, preferably one to several, and more preferably 1 to 10, 1 to 5, 1 to 3, or 1 or 2 amino acids have been replaced, deleted, added, or inserted in the acid sequence of a protein encoded by the gene.

Preferred examples of the gene expression product of the present invention include a protein comprising an amino acid sequence encoded by the above gene (nucleic acid sequence), and a protein with an amino acid sequence for which 1 to 3, and preferably 1 or 2 amino acids have been replaced in said protein. A protein with an amino acid sequence encoded by the above gene (nucleic acid sequence) can be cited as a yet more preferred example.

<2> Peptide of the Present Invention

In one embodiment, the peptide of the present invention includes a partial peptide of a protein encoded by a gene selected from the group consisting of PVT1, SUV39H2, ZNF724P, SNRNP40, and DYRK4, the peptide binding to an MHC, and in particular to an HLA; it is preferably a peptide that is presented as an antigen by means of an MHC, in particular an HLA, and more preferably a peptide that is presented as an antigen by means of an MHC, in particular an HLA, and can induce a CTL. There are several types of HLA; the peptide of the present invention preferably can bind to an HLA class I, and more preferably can bind to HLA-A24. The peptide of the present invention may be subjected to a treatment such as processing prior to binding to an MHC, and a peptide that forms an epitope peptide as a result of such a treatment is also included in the peptide of the present invention. Therefore, the amino acid length of the peptide of the present invention is not particularly limited as long as it is a sequence including an amino acid sequence of an epitope peptide. However, it is preferable that the peptide of the present invention itself is an epitope peptide, and therefore the amino acid length is preferably on the order of about 8 to 14 amino acids, more preferably on the order of about 8 to 11 amino acids, and particularly preferably on the order of about 9 to about 11 amino acids.

An epitope peptide that binds to an HLA class I, which is a human MHC class I, has a length of about 8 to 14 amino acids, and preferably a length of about 9 to 11 amino acids, and is known to have an HLA-specific binding motif in the sequence. For example, a peptide binding to HLA-A02 has a binding motif in which the second amino acid from the N terminal is leucine, isoleucine, or methionine and/or the amino acid at the C terminal is valine, leucine, or isoleucine, and a peptide binding to HLA-A24 has a binding motif in which the second amino acid from the N terminal is tyrosine, phenylalanine, methionine, or tryptophan and/or the amino acid at the C terminal is leucine, isoleucine, or phenylalanine.

Therefore, in a preferred embodiment, the peptide of the present invention includes an epitope peptide that is a partial peptide of a protein encoded by a gene selected from the group consisting of PVT1, SUV39H2, ZNF724P, SNRNP40, and DYRK4, with 8 to 14 consecutive amino acids in the amino acid sequence of said protein, the second amino acid from the N terminal being tyrosine, phenylalanine, methionine, or tryptophan and/or the amino acid at the C terminal being leucine, isoleucine, or phenylalanine, and more preferably is the epitope peptide itself. Among them, an epitope peptide with an amino acid sequence represented by any of SEQ ID No: 1, SEQ ID No: 2, SEQ ID No: 3, SEQ ID No: 4, or SEQ ID No: 5 is particularly preferable.

Furthermore, in another preferred embodiment, the partial peptide includes an epitope peptide, the second amino acid from the N terminal being replaced by tyrosine, phenylalanine, methionine, or tryptophan and/or the amino acid at the C terminal being by leucine, isoleucine, or replaced phenylalanine, and more preferably is the epitope peptide itself. Among them, an epitope peptide with an amino acid sequence represented by any of SEQ ID No: 1, SEQ ID NO: 2, SEQ ID No: 3, SEQ ID No: 4, or SEQ ID No: 5, the second amino acid from the N terminal being replaced by tyrosine, phenylalanine, methionine, or tryptophan and/or the amino acid at the C terminal being replaced by leucine, isoleucine, or phenylalanine is particularly preferable.

The peptide of the present invention may have its N terminal and/or C terminal modified. Specific examples of the modification include N-alkanoylation (for example, acetylation), N-alkylation (for example, methylation), a C-terminal alkyl ester (for example, an ethyl ester), and a C-terminal amide (for example a carboxamide).

Synthesis of the peptide of the present invention may be carried out in accordance with known methods used in normal peptide chemistry. Such known methods includes methods described in the literature (Peptide Synthesis, Interscience, New York, 1966; The Proteins, Vol. 2, Academic Press Inc., New York, 1976; Peptide Synthesis, Maruzen Co., Ltd., 1975; Basics and Experiments of Peptide Synthesis, Maruzen Co., Ltd., 1985; Development of Pharmaceuticals Seq. Vol. 14 Peptide Synthesis, Hirokawa Shoten Co., 1991, these publications forming part of the present application by reference), etc.

With regard to the peptide of the present invention, in vivo activity can be confirmed by subjecting it to a CTL induction method, which is described later, an assay using an animal model for humans (WO02/47474, Int J. Cancer: 100, 565-570 (2002)), etc.

The peptide of the present invention further includes a peptide in which a plurality of epitope peptides including at least one of the peptides of the present invention are linked (polyepitope peptide). Therefore, specific examples of the peptide of the present invention include a peptide that is the above polyepitope peptide and has CTL-inducing activity.

The polyepitope peptide of the present invention may specifically be defined as (i) a peptide in which the peptide of the present invention (epitope peptide) and any one or more CTL epitope peptides other than the peptide of the present invention are linked directly or via a spacer as appropriate, (ii) a peptide in which the peptide of the present invention and any one or more helper epitope peptides are linked directly or via a spacer as appropriate, or (iii) a peptide in which a polyepitope peptide described in (i) above and further one or more helper epitope peptides are linked directly or via a spacer as appropriate, the peptide being subjected to processing within an antigen-presenting cell, and the epitope peptide thus formed being presented on the antigen-presenting cell, thus leading to CTL-inducing activity.

The CTL epitope peptide other than the peptide of the present invention in (i) is not particularly limited; specific examples include a human ASB4-derived epitope peptide and a human OR7C1- or human DNAJB8-derived epitope peptide (for example, a peptide described in WO2010/050190), and a human FAM83B-derived epitope peptide (International Patent Application PCT/JP2014/076625), etc.

The spacer is not particularly limited as long as it does not adversely affect to the processing within an antigen-presenting cell, and is preferably a linker that is linked to each epitope peptide via a peptide bond, examples including a peptide linker in which several amino acids are linked and a linker having an amino group and a carboxyl group at each end. Specific examples include a glycine linker or a PEG (polyethylene glycol) linker; examples of the glycine linker include polyglycine (for example a peptide consisting of six glycines; Cancer Sci, Vol. 103, p. 150-153), and examples of the PEG linker include a linker derived from a compound having an amino group and a carboxy group at each end of PEG (for example, $H_2N$—$(CH_2)_2$—$(OCH_2CH_2)_3$—COOH; Angew. Chem. Int. Ed. 2008, 47, 7551-7556).

With regard to the epitope peptide of the present invention contained in the polyepitope peptide of the present invention, one or more types may be selected. That is, a plurality of identical epitope peptides may be linked, or a plurality of different epitope peptides may be linked. Naturally, even when two or more types of epitope peptides are selected, a plurality of one or more types of selected epitope peptides may be linked. Similarly, with regard to the epitope peptide other than the peptide of the present invention, a plurality of types and/or a plurality of epitope peptides may be linked. The polyepitope peptide of the present invention may be one in which 2 to 12 epitope peptides are linked, is preferably one in which 2, 3, 4, 5, 6, 7, 8, 9, 10, 11, or 12 epitope peptides are linked, and is most preferably one in which 2 epitope peptides are linked.

When the epitope peptide that is linked to the peptide of the present invention is a helper epitope peptide, examples of the helper epitope peptide used include hepatitis B virus-derived HBVc128-140 and tetanus toxin-derived TT947-967. The length of the helper epitope peptide is on the order of 13 to 30 amino acids, and preferably on the order of 13 to 17 amino acids.

Such a peptide in which a plurality of epitope peptides are linked (polyepitope peptide) may also be produced by a standard peptide method synthesis as described above. Furthermore, based on information regarding the sequence of a polynucleotide encoding such a polyepitope peptide in which a plurality of epitope peptides are linked, it may be produced using standard DNA synthesis and genetic engineering methods.

That is, said polynucleotide is inserted into a known expression vector, a host cell is transformed by means of the recombinant expression vector thus obtained to give a transformant, the transformant is cultured, and the target polyepitope peptide in which a plurality of epitopes are linked can be produced by recovery from the culture. These methods may be carried out in accordance with methods described in the literature as described above (Molecular Cloning, T. Maniatis et al., CSH Laboratory (1983), DNA Cloning, D M. Glover, IRL PRESS (1985)).

The polyepitope peptide thus produced in which a plurality of epitope peptides are linked is subjected to the above in vitro assay or an in vivo assay using an animal model for humans described in WO02/47474 and Int J. Cancer: 100, 565-570 (2002) (these publications forming part of the present application by reference), etc., thus enabling CTL-inducing activity to be confirmed.

The peptide of the present invention (including the polyepitope peptide) is useful for the prevention and/or therapy of a cancer, etc. as described in the present specification, and may be an active ingredient of pharmaceutical composition. Furthermore, the peptide of the present invention may be for the prevention and/or therapy of a cancer. Moreover, the present invention also relates to use of the peptide of the present invention in the production of a medicament for the prevention and/or therapy of a cancer.

<3> Polynucleotide of the Present Invention

The polynucleotide of the present invention includes a polynucleotide that encodes at least one of the peptides of the present invention. The polynucleotide of the present invention may be any of CDNA, mRNA, CRNA, or synthetic DNA. It may have either a single strand or a double strand configuration. Specific examples include, but are not limited to, a polynucleotide with a nucleotide sequence encoding an amino acid sequence that is a partial peptide of a protein encoded by a gene selected from the group consisting of PVT1, SUV39H2, ZNF724P, SNRNP40, and DYRK4 and is predicted to have binding properties using an MHC and peptide binding prediction program, such as BIMAS (http://www-bimas.cit.nih.gov/molbio/hla_bind/), SYFPEITHI (http://www.syfpeithi.de/) and IEDB (MHC-I processing predictions; http://www.iedb.org/). Other specific examples include a polynucleotide with a nucleotide sequence encoding an amino acid sequence described in SEQ ID Nos: 1-5, and a polynucleotide with a nucleotide sequence encoding so that it can express a polyepitope peptide in which any two or more peptides selected from SEQ ID Nos: 1-5 are linked or a peptide selected from SEQ ID Nos: 1-5 and a helper epitope are linked.

The polynucleotide of the present invention may take on either a single strand or a double strand configuration. When the polynucleotide of the present invention is a double strand, a recombinant expression vector expressing the peptide of the present invention may be produced by inserting the polynucleotide of the present invention into an expression vector. That is, the scope of the polynucleotide of the present invention includes a recombinant expression vector produced by inserting the double strand polynucleotide of the present invention into an expression vector.

The polynucleotide of the present invention is useful for the prevention and/or therapy of a cancer, etc. as described in the present specification, and may be an active ingredient of a pharmaceutical composition. Furthermore, the polynucleotide of the present invention may be for the prevention and/or therapy of a cancer. Moreover, the present invention also relates to use of the polynucleotide of the present invention in the production of a medicament 1 the prevention and/or therapy of a cancer.

With regard to the expression vector used in the present invention, various types may be used according to the host used, the intended application, etc., and a person skilled in the art may select it as appropriate. Examples of expression vectors that can be used in the present invention include a plasmid, a phage vector, and a virus vector. For example, when the host is *Escherichia coli*, examples of the vector include plasmid vectors such as pUC118, pUC119, pBR322, and pCR3 and phage vectors such as ΔZAPII and Δgt11. When the host is a yeast, examples of the vector include pYES2 and pYEUra3. When the host is an insect cell, examples include pAcSGHisNT-A. When the host is an animal cell, examples include plasmid vectors such as pCEP4, pKCR, pCDM8, pGL2, pcDNA3.1, pRc/RSV, and pRc/CMV and virus vectors such as a and an adeno-retrovirus vector, an adenovirus vector, associated virus vector.

The vector may have as appropriate a factor such as a promoter capable of inducing expression, a gene encoding a signal sequence, a selection marker gene, or a terminator. Furthermore, in order to make isolation and purification easy, a sequence for expression as a fusion protein with thioredoxin, a His tag, GST (glutathione S-transferase), etc. may be added. In this case, a GST fusion protein vector (pGEX4T, etc.) having an appropriate promoter (lac, tac, trc, trp, CMV, SV40 early promoter, etc.) that functions within a host cell, a vector having a tag sequence such as Myc or His (pcDNA3.1/Myc-His, etc.) and, furthermore, a vector expressing a fusion protein with thioredoxin and a His tag (pET32a), etc. may be used.

Transforming a host with the expression vector prepared as above enables a transformed cell containing the expression vector to be prepared. Therefore, the present invention includes a gene transfer composition including the expression vector.

The host used for transformation may be any cell as long as the function of the polypeptide of the present invention is not impaired, and examples include an *Escherichia coli*, a yeast, an insect cell, and an animal cell. Examples of the *Escherichia coli* include *E. coli* K-12 strain HB101, C600, JM109, DH5α, and AD494 (DE3). Examples of the yeast include *Saccharomyces cerevisiae*. Examples of the animal cell include L929 cells, BALB/c3T3 cells, C127 cells, CHO cells, COS cells, Vero cells, Hela cells, and 293-EBNA cells. Examples of the insect cell include sf9.

As a method for introducing an expression vector into a host cell, a standard introduction method suitable for the host cell may be used. Specific examples include a calcium phosphate method, a DEAE-dextran method, an electroporation method, and a method using a lipid for gene transfer (Lipofectamine, Lipofectin; Gibco-BRL). After introduction, culturing is carried out in a standard medium containing a selection marker, thus enabling a transformed cell in which the expression vector has been introduced into the host cell to be selected.

Continuing culturing the transformed cell thus obtained under suitable conditions enables the peptide of the present invention to be produced. The peptide thus obtained may be further isolated and purified by usual biochemical purification means. Examples of purification means include salting out, ion-exchange chromatography, adsorption chromatography, affinity chromatography, and gel filtration chromatography. When the peptide of the present invention is expressed as a fusion protein with a thioredoxin, a His tag, a GST, etc. as described above, isolation and purification may be carried out by a purification method utilizing the properties of the fusion protein or the tag.

The polynucleotide encoding the peptide of the present invention may have a DNA configuration or an RNA configuration. These polynucleotides of the present invention may be easily produced by standard methods known in the present technical field based on amino acid sequence information of the peptide of the present invention and DNA sequence information encoded thereby. Specifically, it may be produced by standard DNA synthesis, amplification by means of PCR, etc.

The polynucleotide encoding the peptide of the present invention includes a polynucleotide encoding the epitope peptide.

<4> CTL Inducer/Pharmaceutical Composition Comprising Peptide of the Present Invention as Active Ingredient The peptide of the present invention has CTL-inducing activity and can be a CTL inducer as a tumor antigen peptide. Furthermore, as described above, the present inventors have found for the first time that a protein encoded by a gene selected from the group consisting of PVT1, SUV39H2, ZNF724P, SNRNP40, and DYRK4 is a tumor antigen and a peptide derived from the protein binds to an HLA class I antigen, forms a complex on the tumor cell surface, is transported to the cell surface, and is presented as an antigen. Therefore, a protein encoded by a gene selected from the group consisting of PVT1, SUV39H2, ZNF724P, SNRNP40, and DYRK4 itself also can become a CTL inducer.

That is, peripheral blood lymphocytes are isolated from a person who is positive for an HLA-A24 antigen, they are stimulated in vitro by adding the peptide of the present invention and/or a protein encoded by a gene selected from the group consisting of PVT1, SUV39H2, ZNF724P, SNRNP40, and DYRK4, and CTLs that specifically recognize an HLA-A24 antigen-positive cell that have been pulsed with the peptide can be induced (J. Immunol., 154, p. 2257, 1995). The presence or absence of CTL induction may be confirmed by measuring for example the amount of various cytokines (for example IFN-γ) produced by CTLs when reacting with an antigen peptide-presenting cell, by means of for example an ELISA method, etc. It may also be confirmed by a method for measuring CTL toxicity toward an antigen peptide-presenting cell labeled with $^{51}$Cr ($^{51}$Cr release assay, Int. J. Cancer, 58: p317, 1994).

Furthermore, a CTL clone may be established by a method described in Int. J. Cancer, 39, 390-396, 1987, N. Eng. J. Med, 333, 1038-1044, 1995, etc.

A CTL induced by the peptide of the present invention and/or a protein encoded by a gene selected from the group consisting of PVT1, SUV39H2, ZNF724P, SNRNP40, and DYRK4 has cytotoxic action toward a cell presenting the peptide of the present invention and/or another epitope peptide derived from a protein encoded by a gene selected from the group consisting of PVT1, SUV39H2, ZNF724P, SNRNP40, and DYRK4 as an antigen and the ability to produce a lymphokine. Since the peptide of the present invention is a tumor antigen peptide as described above, and the protein encoded by a gene selected from the group consisting of PVT1, SUV39H2, ZNF724P, SNRNP40, and DYRK4 is decomposed within a cell to thus form a tumor antigen peptide, it can exhibit an anti-tumor action, and preferably an anti-cancer action, via the above functions. Therefore, the peptide of the present invention and/or a protein encoded by a gene selected from the group consisting of PVT1, SUV39H2, ZNF724P, SNRNP40, and DYRK4 and a CTL induced thereby can be an active ingredient of a medicament or a pharmaceutical composition for the prevention and/or therapy of a cancer.

When a CTL inducer containing the peptide of the present invention and/or a protein encoded by a gene selected from the group consisting of PVT1, SUV39H2, ZNF724P, SNRNP40, and DYRK4 as an active ingredient is administered to a cancer patient, the peptide of the present invention and/or the epitope peptide derived from a protein encoded by a gene selected from the group consisting of PVT1, SUV39H2, ZNF724P, SNRNP40, and DYRK4 is presented on an HLA antigen, preferably an HLA-A24 cell, a antigen, of an antigen-presenting CTL that specifically recognizes a complex of the HLA antigen and the presented peptide proliferates and destroys the cancer cells, and as a result, the prevention and/or therapy of the cancer is possible. Therefore, a CTL inducer containing the peptide of the present invention and/or a protein encoded by a gene selected from the group consisting of PVT1, SUV39H2, ZNF724P, SNRNP40, and DYRK4 as an active ingredient can preferably be used for a subject who is positive for an HLA-A24 antigen and who has a cancer positive for PVT1, SUV39H2, ZNF724P, SNRNP40, or DYRK4. Examples of cancers positive for PVT1, SUV39H2, ZNF724P, SNRNP40, or DYRK4 include cancers (tumors) such as colon cancer, lung cancer, breast cancer, myeloma, oral cancer, pancreatic cancer, skin cancer, and prostate cancer, and the CTL inducer of the present invention may be used for the prevention and/or therapy of such cancers.

The 'prevention' of a cancer includes not only preventing a patient from having a cancer but also prevention of recurrence in a patient who has been subjected to surgery to remove a primary tumor and prevention of metastasis of a tumor that could not be completely removed by a cancer therapy such as surgery, radiotherapy, drug therapy, etc. Furthermore, the 'therapy' of a cancer includes not only curing and improvement of the symptoms of a cancer that reduces the size of the cancer but also prevention of progress such as suppression of cancer cell proliferation, tumor enlargement, or metastasis of cancer cells from a primary focus.

A CTL inducer containing the peptide of the present invention and/or a protein encoded by a gene selected from the group consisting of PVT1, SUV39H2, ZNF724P, SNRNP40, and DYRK4 as an active ingredient is for example particularly effective for an HLA-A24-positive cancer patient who has a cancer positive for PVT1, SUV39H2, ZNF724P, SNRNP40, or DYRK4. Specifically, it may be used for the prevention or therapy of a cancer (tumor) such as for example colon cancer, lung cancer, breast cancer, myeloma, oral cancer, pancreatic cancer, skin cancer, and prostate cancer. Therefore, a pharmaceutical composition containing the peptide of the present invention and/or a protein encoded by a gene selected from the group consisting of PVT1, SUV39H2, ZNF724P, SNRNP40, and DYRK4 as an active ingredient is also included in the present invention. Such a pharmaceutical composition is preferably a composition for the prevention and/or therapy of a cancer, that is, a preventive and/or therapeutic agent for cancer. Furthermore, since the pharmaceutical composition of the present invention carries out prevention and/or therapy of a cancer by inducing a CTL that is specific to a cancer cell, that is, activating cell-mediated immunity that is specific to a cancer cell, it is preferably a vaccine for the prevention and/or therapy of a cancer.

A pharmaceutical composition containing the peptide of the present invention as an active ingredient may be one that contains a single CTL epitope (the peptide of the present invention) as an active ingredient or one that contains as an active ingredient a polyepitope peptide having another peptide (CTL epitope or helper epitope) linked thereto. In recent years, it has been shown that a polyepitope peptide having a plurality of linked CTL epitopes (antigen peptides) has activity in efficiently inducing CTLs in vivo. For example, Journal of Immunology 1998, 161:3186-3194 (this publication forms part of the present application by reference) describes the induction in vivo of a CTL that is specific to each CTL epitope by means of an approximately 30mer polyepitope peptide in which cancer antigen protein PSA-derived HLA-A2-, -A3-, -A11-, and -B53-restricted CTL epitopes (antigen peptides) are linked. It is also shown that a polyepitope peptide in which a CTL epitope and a helper epitope are linked efficiently induces a CTL. When administered in the configuration of such a polyepitope peptide, the polyepitope peptide is incorporated into an antigen-presenting cell, and individual antigen peptides that have been formed by intracellular degradation subsequently bind to an HLA antigen to thus form a complex, this complex is presented on the antigen-presenting cell surface at high density, a CTL specific to this complex proliferates efficiently in the body, and cancer cells are destroyed. In this way, the therapy or prevention of a cancer is promoted.

A pharmaceutical composition containing the peptide of the present invention and/or a protein encoded by a gene selected from the group consisting of PVT1, SUV39H2, ZNF724P, SNRNP40, and DYRK4 as an active ingredient may be administered as a mixture with a pharmaceutically acceptable carrier, for example an appropriate adjuvant, or in combination therewith, so as to establish cell-mediated immunity effectively.

As the adjuvant, an adjuvant known in the present technical field such as one described in the literature (for example, Clin Infect Dis.: S266-70, 2000) may be applied, and specific examples include a gel type such as aluminum hydroxide, aluminum phosphate, or calcium phosphate, a bacterial type such as CpG, monophosphoryl lipid A (MPL), cholera toxin, *Escherichia coli* heat-labile toxin, pertussis toxin, or muramyl dipeptide (MDP), an oil emulsion type (emulsion preparation) such as Freund's incomplete adjuvant, MF59, or SAF, a macromolecular nanoparticle type such as an immunostimulatory complex (ISCOMs), a liposome, biodegradable microspheres, or saponin-derived QS-21, a synthetic type such as a nonionic block copolymer, a muramyl peptide analog, a polyphosphazene, or a synthetic polynucleotide, and a cytokine type such as IFN-γ, IL-2, or IL-12.

Furthermore, the dosage form of a CTL inducer/pharmaceutical composition containing the peptide of the present invention and/or a protein encoded by a gene selected from the group consisting of PVT1, SUV39H2, ZNF724P, SNRNP40, and DYRK4 as an active ingredient is not particularly limited, and examples include an oil emulsion (emulsion formulation), macromolecular nanoparticles, a liposome formulation, a particulate formulation bonded to beads having a diameter of a few μm, a lipid-bonded formulation, a microsphere formulation, and a microcapsule formulation.

Examples of an administration method include any known administration method such as intradermal administration, subcutaneous administration, intramuscular administration, or intravenous administration. The dose of the peptide of the present invention in a preparation may be adjusted as appropriate according to the disease that is the target of therapy, the age and body weight of the patient, etc., but it is usually 0.0001 mg to 1000 mg, preferably 0.001 mg to 1000 mg, and more preferably 0.1 mg to 10 mg, this being preferably administered once in a few days to a few months.

As a method for making the peptide of the present invention actually act as a medicament, there is an in vivo method in which the peptide is directly introduced into the body as well as an ex vivo method in which a specific type of cell is collected from a person, the peptide of the present invention is made to act thereon in vitro, and the cells are returned into the body (Nikkei Science, April 1994, pp. 20-45, Gekkan Yakuji, 36 (1), 23-48 (1994), Experimental Medicine Special Edition, 12 (15), (1994), references quoted therein, etc., these publications of present forming part the application by reference), and a person skilled in the art can select a cell, an administration method, an administration configuration, and a dose appropriate for such a method.

<5> CTL Inducer/Pharmaceutical Composition Containing the Polynucleotide of the Present Invention as Active Ingredient Since a cell in which the polynucleotide of the present invention and/or a polynucleotide encoding a protein selected from the group consisting of PVT1 protein, SUV39H2 protein, ZNF724P protein, SNRNP40 protein, and DYRK4 protein is expressed becomes a cell that presents the peptide of the present invention and/or another epitope peptide derived from a protein encoded by a gene selected from the group consisting of PVT1, SUV39H2, ZNF724P, SNRNP40, and DYRK4 as an antigen, it has the feature that it is recognized by a T cell via a T cell receptor. Therefore, the polynucleotide of the present invention and/or a polynucleotide encoding a protein selected from the group consisting of PVT1 protein, SUV39H2 protein, ZNF724P protein, SNRNP40 protein, and DYRK4 protein can also become a CTL inducer. An induced CTL can exhibit, in the same way as for a CTL induced by the peptide of the present invention and/or a protein encoded by a gene selected from the group consisting of PVT1, SUV39H2, ZNF724P, SNRNP40, and DYRK4, an anti-tumor action via a cytotoxic action or the production of a lymphokine, and preferably an anti-cancer action. Therefore, the polynucleotide of the present invention and/or a polynucleotide encoding a protein selected from the group consisting of PVT1 protein, SUV39H2 protein, ZNF724P protein, SNRNP40 protein, and DYRK4 protein can be an active ingredient of a medicament or a pharmaceutical composition for the therapy or prevention of a cancer. A CTL inducer containing the polynucleotide of the present invention and/or a polynucleotide encoding a protein selected from the group consisting of PVT1 protein, SUV39H2 protein, ZNF724P protein, SNRNP40 protein, and DYRK4 protein as an active ingredient makes possible the therapy and/or prevention of a cancer by for example administering the polynucleotide of the present invention and/or a polynucleotide encoding a protein selected from the group consisting of PVT1 protein, SUV39H2 protein, ZNF724P protein, SNRNP40 protein, and DYRK4 protein to a cancer patient and expressing them in the cancer patient.

For example, when the polynucleotide of the present invention and/or a polynucleotide encoding a protein selected from the group consisting of PVT1 protein, SUV39H2 protein, ZNF724P protein, SNRNP40 protein, and DYRK4 protein incorporated into an expression vector is administered to a cancer patient by the method below, a tumor antigen peptide is highly expressed within antigen-presenting cells. The tumor antigen peptide thus produced subsequently binds to an HLA antigen such as an HLA-A24 antigen to form a complex, this complex is presented at high density on the antigen-presenting cell surface, cancer-specific CTLs proliferate efficiently in the body, and the cancer cells are destroyed. As described above, the therapy or prevention of a cancer achieved. Therefore, a pharmaceutical composition containing the polynucleotide of the present invention and/or a polynucleotide encoding a protein selected from the group consisting of PVT1 protein, SUV39H2 protein, ZNF724P protein, SNRNP40 protein, and DYRK4 protein is also included in the present invention. Such a pharmaceutical composition is preferably a composition for the prevention and/or therapy of a cancer, that is, a preventive and/or therapeutic agent for cancer. Furthermore, since the pharmaceutical composition of the present invention carries out prevention and/or therapy of a cancer by inducing a CTL that is specific to a cancer cell (preferably a cancer stem cell), that is, activating cell-mediated immunity that is specific to a cancer cell, it is preferably a vaccine for the prevention and/or therapy of a cancer.

The CTL inducer/pharmaceutical composition containing the polynucleotide of the present invention as an active ingredient may preferably be used for an HLA-A24 antigen-positive subject who has a cancer positive for PVT1, SUV39H2, ZNF724P, SNRNP40, or DYRK4. Examples of the cancer positive for PVT1, SUV39H2, ZNF724P, SNRNP40, or DYRK4 include cancers (tumors) such as colon cancer, lung cancer, breast cancer, myeloma, oral cancer, pancreatic cancer, skin cancer, and prostate cancer, and the CTL inducer of the present invention may be used for the prevention or therapy of these cancers.

As a method for administering the polynucleotide of the present invention and/or a polynucleotide encoding a protein selected from the group consisting of PVT1 protein, SUV39H2 protein, ZNF724P protein, SNRNP40 protein, and DYRK4 protein and incorporating it into a cell, any method such as a method involving a virus vector and other methods (Nikkei Science, 1994 April, pp. 20-45, Gekkan Yakuji, 36 (1), 23-48 (1994), Experimental Medicine Special Edition, 12 (15), (1994), references quoted therein, etc., these publications forming part of the present application by reference) may be employed. Therefore, in an embodiment of the pharmaceutical composition of the present invention, a vector containing the polynucleotide of the present invention and/or a polynucleotide encoding a protein selected from the group consisting of PVT1 protein, SUV39H2 protein, ZNF724P protein, SNRNP40 protein, and DYRK4 protein is contained as an active ingredient.

Examples of the method involving a virus vector include a method in which the DNA of the present invention is integrated into for example a DNA virus or RNA virus such as a retrovirus, adenovirus, adeno-associated virus, herpes virus, vaccinia virus, poxvirus, poliovirus, or sindbis virus, and incorporation is carried out. Among them, a method involving a retrovirus, adenovirus, adeno-associated virus, vaccinia virus, etc. is particularly preferable.

Examples of other methods include a method in which an expression plasmid is directly administered intramuscularly (DNA vaccine method), a liposome method, a lipofectin method, a microinjection method, a calcium phosphate method, and an electroporation method; a DNA vaccine method and a liposome method are particularly preferable.

In order to make the polynucleotide of the present invention and/or a polynucleotide encoding a protein selected from the group consisting of PVT1 protein, SUV39H2 protein, ZNF724P protein, SNRNP40 protein, and DYRK4 protein actually act as a medicament, there are an in vivo method in which the polynucleotide is directly introduced into the body and an ex vivo method in which a specific type of cell is collected from a person, the polynucleotide of the present invention is incorporated into the cells in vitro, and the cells are returned into the body (Nikkei Science, 1994 April, pp. 20-45, Gekkan Yakuji, 36 (1), 23-48 (1994), Experimental Medicine Special Edition, 12 (15), (1994), references quoted therein, etc., these publications forming part of the present application by reference). An in vivo method is more preferable.

When the polynucleotide of the present invention and/or a polynucleotide encoding a protein selected from the group consisting of PVT1 protein, SUV39H2 protein, ZNF724P protein, SNRNP40 protein, and DYRK4 protein is administered by an in vivo method, administration may be carried out by selecting as appropriate an administration route and an administration form according to the disease that is the target of therapy, the symptoms, etc. For example, administration may be carried out in a form that can be injected into a vein, an artery, subcutaneously, intradermally, intramuscularly, etc. When administration is carried out by an in vivo method, for example, a formulation form such as a liquid may be employed, but it is usually made into an injection, etc. containing the polynucleotide of the present invention, which is an active ingredient, and a pharmaceutically acceptable carrier may be added as necessary. With regard to a liposome or a membrane fusion liposome (Sendai virus (HVJ)-liposome, etc.) containing the polynucleotide of the present invention, a liposome preparation such as a suspension, a frozen agent, or a centrifugation-concentrated frozen agent may be employed.

The content the polynucleotide of the present invention in a formulation may be adjusted as appropriate according to the disease that is the target of therapy, the age and body weight of the patient, etc.; it is usually 0.0001 mg to 100 mg as a polynucleotide content, and preferably 0.001 mg to 10 mg of the polynucleotide of the present invention, it preferably being administered once in a few days to a few months.

A person skilled in the art can appropriately select a suitable cell, vector, administration method, administration form, and dose.

Furthermore, in recent years, it has been shown that a polynucleotide encoding a polyepitope peptide having a plurality of linked CTL epitopes (tumor antigen peptides) and a polynucleotide encoding a polyepitope peptide having a CTL epitope and a helper epitope that are linked have activity in efficiently inducing CTLs in vivo. For example, Journal of Immunology 1999, 162:3915-3925 (this publication forms part of the present application by reference) reports that DNA encoding an epitope peptide (minigene) having six types of HBV-derived HLA-A2-restricted antigen peptides, three types of HLA-A11-restricted antigen peptides, and a helper epitope that are linked has induced CTLs for each epitope in vivo effectively.

Therefore, a CTL inducer active ingredient can be made by incorporating into an appropriate expression vector a polynucleotide prepared by linking one or more types of polynucleotide encoding the peptide of the present invention, and in some cases also linking a polynucleotide encoding another peptide. Such a CTL inducer can also employ the same administration method and administration form as described above.

Furthermore, it has been found in recent years that cancer cells avoid elimination by the immune system by shading the attack by immune cells, and such shading utilizes a mechanism called 'immune checkpoint', which is naturally present in order to suppress an excessive autoimmune reaction and damage to normal tissue. Therefore, the attack by immune cells can be made effective by suppressing the immune checkpoint function in cancer cells. Since the pharmaceutical composition of the present invention exhibits an anti-tumor effect by inducing a tumor-specific immune cell, a higher therapeutic effect can be exhibited by suppressing the immune checkpoint function at the same time. Therefore, in a preferred embodiment, the pharmaceutical composition of the present invention is used together with an immune checkpoint inhibitor.

In the present invention, when one agent A and another agent B are 'used together' or 'used in combination', it means a state in which, while agent A is exhibiting an effect, agent B exhibits an effect. Therefore, agent B may be administered at the same time as agent A is administered, or agent B may be administered at a certain time after agent A is administered. Furthermore, agent A and agent B may be in the same administration form or may be in different administration forms. Moreover, as long as the effect of agent A or agent B is not lost, agent A and agent B may be mixed as one composition.

As an immune checkpoint inhibitor in the present embodiment, any agent known as an immune checkpoint inhibitor may be used as long as it does not inhibit the ability of the composition of the present invention in inducing a CTL. Examples of known immune checkpoint inhibitors include, but are not limited to, anti-PD-1 antibody, anti-PD-L1 antibody, anti-CTLA-4 antibody, anti-TIM-3 antibody, anti-LAG-3 antibody, anti-B7-H3 antibody, anti-B7-H4 antibody, anti-B7-H5 antibody, and anti-TIGIT antibody.

<6> Antigen-Presenting Cell of the Present Invention

The peptide and polynucleotide of the present invention described above may be utilized for example in vitro as follows. That is, either of the peptide and the polynucleotide of the present invention cells having antigen-presenting ability are brought into contact with each other in vitro, thus enabling antigen-presenting cells that present the antigen peptide of the present invention as an antigen to be prepared. Therefore, one embodiment of the present invention provides an antigen-presenting cell that presents on the cell surface a complex of an HLA antigen, preferably an HLA-A24 antigen, and the peptide of the present invention, and a method for producing same. As described above, the peptide and the polynucleotide of the present invention can be utilized for the prevention and/or therapy of a cancer. Therefore, the antigen-presenting cell or the production method therefor of the present embodiment preferably utilizes an isolated cell that is derived from a cancer patient. Specifically, an antigen-presenting cell presenting a complex of an HLA antigen, and preferably an HLA-A24 antigen, and the peptide of the present invention on the cell surface of a cancer patient-derived isolated cell having antigen-presenting ability is produced by bringing the cell into contact with either the peptide or the polynucleotide of the present invention in vitro.

The 'cell having antigen-presenting ability' is not particularly limited as long as it is a cell expressing on the cell surface an MHC, preferably an HLA, and more preferably an HLA-A24 antigen, that can present the peptide of the present invention, and among them it is preferably a professional antigen-presenting cell, and particularly preferably a dendritic cell, which is considered to have high antigen-presenting ability.

Furthermore, with regard to a substance that is added in order to prepare the antigen-presenting cell of the present invention from the cell having an antigen-presenting ability, it may be either the peptide or the polynucleotide of the present invention.

The antigen-presenting cell of the present invention is obtained by for example isolating cells having antigen-presenting ability from a cancer patient, and pulsing the cells with the peptide of the present invention in vitro so as to make them present a complex of an HLA-A24 antigen and the peptide of the present invention (Cancer Immunol. Immunother., 46:82, 1998, J. Immunol., 158, p. 1796, 1997, Cancer Res., 59, p. 1184, 1999). When dendritic cells are used, for example, lymphocytes are separated from the peripheral blood of a cancer patient by the Ficoll method, non-adherent cells are then removed, adherent cells are cultured in the presence of GM-CSF and IL-4 to thus induce dendritic cells, and the dendritic cells are cultured and pulsed together with the peptide of the present invention, thus enabling the antigen-presenting cell of the present invention to be prepared.

Furthermore, when the antigen-presenting cell of the present invention is prepared by transfecting the cell having antigen-presenting ability with the polynucleotide of the present invention, the polynucleotide may be in the form of a DNA or the form of an RNA. Specifically, in the case of a DNA, Cancer Res., 56: p. 5672, 1996 or J. Immunol., 161: p. 5607, 1998 (these publications forming part of the present application by reference) may be referred to, and in the case of an RNA, J. Exp. Med., 184: p. 465, 1996 (this publication forming part of the present application by reference) may be referred to.

The antigen-presenting cell can be an active ingredient of a CTL inducer and/or a pharmaceutical composition. The CTL inducer and/or pharmaceutical composition containing the antigen-presenting cell as an active ingredient preferably contain physiological saline, phosphate buffered physiological saline (PBS), a culture medium, etc. in order to maintain the antigen-presenting cell stably. Examples of an administration method include intravenous administration, subcutaneous administration, and intradermal administration. Returning a CTL inducer and/or pharmaceutical composition containing such an antigen-presenting cell as an active ingredient to the body of the patient enables a CTL that is specific to a cancer cell presenting the peptide of the present invention as an antigen to be efficiently induced in the body of a patient having a cancer positive for PVT1, SUV39H2, ZNF724P, SNRNP40, or DYRK4, and as a result the prevention and/or therapy of a PVT1, SUV39H2, ZNF724P, SNRNP40, or DYRK4-positive cancer that presents the peptide of the present invention as an antigen becomes possible.

<7> Cytotoxic T Cell (CTL) of the Present Invention

The peptide and polynucleotide of the present invention may be utilized in vitro for example as follows. That is, a CTL may be induced by bringing either the peptide or the polynucleotide of the present invention into contact with peripheral blood lymphocytes in vitro. Therefore, one embodiment of the present invention provides a CTL that specifically damages a cell that presents the peptide of the present invention as an antigen, and a method for inducing same. As described above, the peptide and polynucleotide of the present invention can be utilized for the prevention and/or therapy of a cancer. Therefore, the CTL and the induction method therefor of the present embodiment preferably utilize peripheral blood lymphocytes derived from a cancer patient. Specifically, a CTL that specifically damages a cell presenting the peptide of the present invention as an antigen is induced by either bringing the peptide or the polynucleotide of the present invention into contact in vitro with peripheral blood lymphocytes derived from a cancer patient.

In a melanoma for example, it has been confirmed that an adoptive immunotherapy in which a large number of intra-tumoral infiltrating T cells from the patient in question are cultured in vitro and returned to the patient has a therapeutic effect (J. Natl. Cancer. Inst., 86: 1159, 1994). Furthermore, in a mouse melanoma it has been confirmed that metastasis is suppressed by stimulating splenocytes in vitro with TRP-2 tumor antigen peptide so as to make CTLs specific to the tumor antigen peptide proliferate and administering the CTLs to a melanoma transplanted mouse (J. Exp. Med., 185: 453, 1997). This is based on the result that specifically recognize a complex of a tumor antigen peptide and an MHC of an antigen-presenting cell proliferate in vitro. It is therefore considered that a therapy in which peripheral blood lymphocytes of a patient are stimulated in vitro using the peptide or the polynucleotide of the present invention to thus increase tumor-specific CTLs and the CTLs are subsequently returned to the patient will be useful.

The CTLs may be an active ingredient of a therapeutic agent or a preventive agent for a cancer. The therapeutic agent or the preventive agent preferably contains physiological saline, phosphate buffered physiological saline (PBS), a culture medium, etc. in order to maintain the CTLs stably. Examples of an administration method include intravenous administration, subcutaneous administration, and intradermal administration. Returning the cancer therapeutic or preventive agent containing such CTLS as an active ingredient to the body of a patient enables the cytotoxic action of the CTLs to cancer cells in the body of a patient having the cancer positive for PVT1, SUV39H2, ZNF724P, SNRNP40, or DYRK4 of the present invention to be promoted, and enables therapy of the cancer by destroying the cancer cells.

The CTL of the present invention can exhibit cytotoxic activity by targeting a complex of an HLA and the peptide of the present invention presented as an antigen on a tumor cell. That is, a T cell receptor (TCR) of the CTL of the present invention recognizes a complex of an HLA and the peptide of the present invention. In recent years, an adoptive immunotherapy has been devised in which a TCR gene that recognizes a specific peptide-HLA complex expressed in a CTL is cloned, this TCR gene is transferred to a CD8$^+$ T cell harvested from a cancer patient to thus artificially produce a CTL, it is cultured on a large scale, and it is then returned to the body of the patient (e.g. Ochi et al., Blood. 2011 Aug. 11; 118 (6): 1495-503, etc.). In the present invention, when an 'artificial CTL' is referred to, it means a CTL that is formed by transferring a gene encoding a TCR that recognizes a complex of a peptide and an HLA to a T cell as described above, and this can also be used in the therapy of a cancer in the same way as for the above natural CTL. Therefore, such an artificial CTL is also included in the CTL of the present invention. In such an embodiment, a TCR that recognizes a complex of the peptide of the present invention and an HLA and that is genetically transferred to an artificial CTL may be modified as appropriate in order to increase the binding affinity toward the complex or the cytotoxic activity. Therefore, the 'artificial CTL' includes a CTL that is formed by appropriately genetically modifying a gene encoding a TCR that recognizes a complex of the peptide of the present invention and an HLA and then transferring the gene to a patient-derived T cell. Preparation of an artificial CTL may employ a method known in the present technical field.

<8> Tumor-Specific CTL-Detecting Agent Using the Peptide of the Present Invention The peptide of the present invention is recognized by a tumor-specific CTL, and is therefore useful as a component of a tumor-specific CTL-detecting agent. Therefore, the present invention also relates to a tumor-specific CTL-detecting agent containing the peptide of the present invention. In one embodiment, the tumor-specific CTL-detecting agent of the present invention contains an HLA multimer (monomer, dimer, tetramer, pentamer, or Dextramer) containing HLA-A24 and the peptide of the present invention.

For example, the HLA tetramer means a tetramer formed by biotinylating a complex (HLA monomer) in which the x chain and the 32 microglobulin of the HLA are associated with a peptide (epitope peptide) and binding it to avidin (Science 279:2103-2106 (1998), Science 274:94-96 (1996)). At present HLA tetramers containing various types of antigen peptides are commercially available (e.g. from Medical & Biological Laboratories Co., Ltd.), and an HLA tetramer containing the peptide of the present invention and HLA-A24 can be easily prepared. Furthermore, an HLA dimer and an HLA pentamer are also based on the same principle, the HLA monomer being formed into the dimer and the pentamer respectively. Therefore, an HLA multimer containing the peptide of the present invention and HLA-A24 is also one embodiment of the present invention.

Specific examples include an HLA tetramer containing a peptide with an amino acid sequence described in any of SEQ ID Nos: 1-5 and HLA-A24. The HLA tetramer is preferably fluorescently labeled so that bound CTLs can be easily screened or detected by known detection means such as flow cytometry or a fluorescence microscope. Specific examples include HLA tetramers labeled with phycoerythrin (PE), fluorescein isothiocyanate (FITC), peridinin chlorophyll protein (PerCP), etc.

Examples of methods for producing an HLA tetramer include those described in the literature, such as Science 279:2103-2106 (1998) and Science 274:94-96 (1996), which are described in brief below.

First, *Escherichia coli* or mammalian cells that can express a protein are transfected with an HLA-A24 a chain expression vector and a 32 microglobulin expression vector and expression is carried out. In this embodiment, it is preferable to use *Escherichia coli* (for example, BL21). The monomer HLA-A24 thus obtained and the peptide of the present invention are mixed to thus form a soluble HLA-peptide complex. Subsequently, the C terminal site sequence of the α chain of HLA-A24 in the HLA-peptide complex is biotinylated with BirA enzyme. This biotinylated HLA-peptide complex and fluorescently-labeled avidin are mixed at a molar ratio of 4:1, thus preparing an HLA tetramer. In each of the above steps, it is preferable to carry out protein purification by means of gel filtration, etc.

<9> Tumor Cell-Detecting Agent

As described above, the present inventors have found that a gene selected from the group consisting of PVT1, SUV39H2, ZNF724P, SNRNP40, and DYRK4 is a cancer testis antigen highly expressed specifically in a tumor cell. That is, it has been found by the present inventors that a gene selected from the group consisting of PVT1, SUV39H2, ZNF724P, SNRNP40, and DYRK4 is a gene whose expression is not observed in normal somatic cells other than the testis, but that is highly expressed in a tumor cell. It has been found from such an observation that a gene selected from the group consisting of PVT1, SUV39H2, ZNF724P, SNRNP40, and DYRK4 can be utilized as a marker for identifying a tumor cell, and in particular a cancer cell. Therefore, one aspect of the present invention relates to a tumor cell-detecting agent that contains a detecting agent for detecting an expression product of a gene selected from the group consisting of PVT1, SUV39H2, ZNF724P, SNRNP40, and DYRK4.

In the present invention, when just 'PVT1, etc.' is used, it means a PVT1 gene, etc. unless otherwise specified. It preferably means a human gene but it may be a homolog thereof.

In the present invention, 'gene expression' means a series of biological reactions initiated by gene transcription, and an 'expression product' is a molecule produced by this series of biological reactions, such as mRNA or an endogenous polypeptide. An endogenous polypeptide, which is a gene expression product, is preferably a protein that is the final product of gene expression.

In the present invention, a 'detecting agent for an expression product of a gene' means an agent for qualitatively and/or quantitatively detecting an expression product of a gene selected from the group consisting of PVT1, SUV39H2, ZNF724P, SNRNP40, and DYRK4.

The tumor cell-detecting agent of the present invention contains a detecting agent for detecting an expression product of a gene selected from the group consisting of PVT1, SUV39H2, ZNF724P, SNRNP40, and DYRK4. When an expression product of a gene selected from the group consisting of PVT1, SUV39H2, ZNF724P, SNRNP40, and DYRK4 is detected in a detection target, it can be determined that the detection target has a tumor cell, i.e., a tumor cell has been detected. The tumor cell-detecting agent of the present invention can be used in vivo or in vitro, but it is preferably used in vitro for a cell population derived from a biological sample (detection target) harvested from a biological individual (test subject). In this case, detection of a tumor cell in a detection target which is a cell population derived from a biological sample means that a tumor cell has been detected in a test subject, i.e., a biological individual from which the biological sample has been harvested, that is, the biological individual has a tumor cell. Therefore, as described herein below, a method for detecting a tumor cell in a test subject using the tumor cell-detecting agent of the present invention, that is, a method for testing whether a test subject has a tumor, is also included in the present invention.

The biological individual as a test subject may be any biological individual as long as it is a biological individual that can have a tumor but is preferably a human or a non-human mammalian individual (e.g. a rodent such as a mouse, a rat, a guinea pig, or a hamster, a primate such as a chimpanzee, an artiodactyl such as a cow, a goat, or a sheep, a perissodactyl such as a horse, and a rabbit, a dog, a cat, etc.), and more preferably a human individual.

The cell population as a detection target can be any biological sample-derived cell population obtained from the test subject but is preferably a cell population derived from a biological sample obtained from a human, and more preferably a cell population containing a cell derived from tissue other than the testis, for example, one or more biological samples selected from the group consisting of heart, brain, placenta, lung, liver, skeletal muscle, kidney, pancreas, spleen, thymus, prostate, testis, ovary, small intestine, large intestine, and blood, in which it has been confirmed that almost no gene selected from the group consisting of PVT1, SUV39H2, ZNF724P, SNRNP40, and DYRK4 is expressed.

The detecting agent for an expression product of a gene selected from the group consisting of PVT1, SUV39H2, ZNF724P, SNRNP40, and DYRK4 contained in the tumor cell-detecting agent of the present invention can be changed depending on the expression product that is to be detected, and a person skilled in the art can select the most suitable one as appropriate. Specifically, for example, when the expression product is an mRNA, any mRNA detection method known in the present technical field may be used, and examples include, but are not limited to, an RT-PCR method, an in situ hybridization method, a Northern blotting method, and real time RT-PCR and, among them, an RT-PCR method is preferable from the viewpoint of high detection sensitivity and ease of experimental technique. For example, when the expression product is an endogenous polypeptide (preferably PVT1 protein, SUV39H2 protein, ZNF724P protein, SNRNP40 protein, and/or DYRK4 protein), examples include, but are not limited to, a Western blotting method and immunohistochemical staining. The detecting agent for an expression product of a gene selected from the group consisting of PVT1, SUV39H2, ZNF724P, SNRNP40, and DYRK4 used can be changed depending on the expression product that is to be detected and the detection method employed, and a person skilled in the art can select the most suitable one as appropriate.

Specifically, for example, when an endogenous polypeptide is to be detected, an antibody specific to PVT1 protein, SUV39H2 protein, ZNF724P protein, SNRNP40 protein and/or DYRK4 protein (preferably a monoclonal antibody), etc. can be cited, and when an mRNA is to be detected, a probe and/or a primer that have a base sequence complementary to the part of the base sequence of a gene selected from the group consisting of PVT1, SUV39H2, ZNF724P, SNRNP40, and DYRK4 can be cited, but examples are not limited to the above. Moreover, the expression product that is to be detected may be a single expression product or a combination of a plurality of expression products.

<10> Antibody that Recognizes the Peptide of the Present Invention

As described above, the peptide of the present invention is presented as a CTL epitope peptide on a tumor cell. In this process, since the peptide of the present invention is presented on a cell surface by forming a complex with an MHC, it is possible to utilize the peptide as a tumor marker by the use of an antibody that recognizes the peptide of the present invention or the complex of said peptide and an MHC. Examples of such an antibody include an antibody (preferably a monoclonal antibody) that specifically recognizes the peptide of the present invention, and a TCR (T cell antigen receptor)—like antibody that recognizes a complex of the peptide of the present invention and an HLA, preferably HLA-A24. Therefore, the present invention also relates to an antibody that recognizes the peptide of the present invention or a complex of said peptide and an MHC, and in particular a monoclonal antibody and a T cell antigen receptor-like antibody.

In the present invention, the 'TCR-like antibody' is a molecule having binding ability (antigen-recognizing ability) similar to TCR to a complex (pMHC) of a fragmented antigen-derived peptide and a major histocompatibility complex (MHC) molecule. For example, as reported in Eur J Immunol. 2004; 34:2919-29, etc., a TCR-like antibody that recognizes a complex of a tumor antigen-derived peptide and an MHC can recognize a cancer cell that is presenting a tumor antigen peptide that can be targeted by a CTL, a dendritic cell that has phagocytized a cancer cell and is presenting a tumor antigen peptide on an MHC class I, etc.

The TCR-like antibody may be prepared by a method described in Eur J Immunol. 2004; 34:2919-29, etc. For example, immunizing an animal such as a mouse with an MHC-peptide complex enables an antibody that is specific to the complex to be obtained. It is also possible to obtain a complex-specific antibody by utilizing a phage display method.

As described above, recognizing the peptide of the present invention and/or MHC complex presenting said peptide enables a tumor cell that presents the MHC complex containing the peptide of the present invention on the cell surface to be detected. Therefore, the present invention also relates to a tumor-detecting agent containing the above-mentioned TCR-like antibody. Furthermore, since the peptide of the present invention is similarly presented on an antigen-presenting cell, particularly a professional antigen-presenting cell such as a dendritic cell, in addition to a tumor cell, the above TCR-like antibodies are also useful for detection of an antigen-presenting cell, etc. presenting the peptide of the present invention.

In the present invention, when referring to an 'antibody', not only immunoglobulin molecules, but also functional fragments of antibodies such as Fab, Fab', F(ab')2, Fv, ScFv, dsFv, diabody and sc(Fv)2 are included. Multimers (for example, dimers, trimers, tetramers, polymers) of these functional fragments are also included in the antibody of the present invention.

In addition, as described above, since the peptide of the present invention is presented as a CTL epitope peptide by a tumor cell, a TCR-like antibody that recognizes said peptide and/or a complex of the peptide of the present invention and an HLA, and preferably a complex with HLA-A24, can bind to said complex present on the cell surface in a subject. When the TCR-like antibody binds to the surface of a tumor cell, the Fc receptor of an effector cell such as a macrophage or an NK cell binds to the Fc site of the antibody, and antibody-dependent cellular cytotoxicity (ADCC) activity involving the effector cell attacking the tumor cell is generated, thereby enabling treatment of the tumor. Therefore, the TCR-like antibody is also useful for the prevention and/or therapy of a cancer. Therefore, the present invention also relates to an agent for the prevention and/or therapy of a cancer that includes the TCR-like antibody of the present invention.

In recent years, bispecific antibodies that are modified to have two antigen binding sites each binding to a different antigen have been developed. Bispecific antibodies in which a cancer cell surface antigen such as an MHC-antigen peptide complex is recognized at one antigen binding site and a lymphocyte surface antigen such as CD3 is recognized at the other antigen binding site are able to restrict and integrate cells having lymphocyte surface antigens such as CTLs and effector cells in the vicinity of cancer cells. Lymphocytes restricted in the vicinity of cancer cells themselves not only exhibit antitumor activity such as ADCC activity, but also activate naive immune cells in an antitumor manner around the cancer cells by secretion of cytokines and the like; they can thus attack cancer cells by exhibiting a bystander effect.

Accordingly, the present invention also encompasses a bispecific antibody which specifically recognizes the peptide of the present invention and/or a complex of said peptide and an HLA, as well as a lymphocyte surface antigen. The lymphocyte surface antigen that is specifically recognized is not particularly limited as long as it is an antigen that is specifically expressed on the surface of a lymphocyte, but it preferably includes CD3, CD16, CD64 and the like. In particular, CD3 is a cell surface antigen involved in the induction of cytotoxic activity of a CTL, and when CD3 binds to an antibody, a CTL can be activated in an HLA-unrestricted manner, without recognizing an HLA-cancer antigen complex; the exhibition of strong cytotoxic activity can thus be expected, which is preferable.

Furthermore, in recent years, a new immune cell therapy has been devised that includes forming a chimeric antigen receptor (CAR) by genetically engineering and modifying a part of a monoclonal antibody specific to a tumor antigen, genetically transferring it to a patient-derived T cell, culturing and amplifying this genetically modified T cell ex vivo, and injecting the genetically modified T cells into the patient (Nat Rev Immunol. 2012; 12: 269-81). Specifically, peripheral blood mononuclear cells harvested from a patient are cultured in the presence of an anti-CD3 antibody and IL-2, etc. to thus activate T cells, and a gene encoding a CAR is introduced into the T cells by the use of a transfection vector such as a retrovirus vector or a lentivirus vector to thus prepare genetically modified T cells.

In the present invention, the 'chimeric antigen receptor' is a chimeric protein molecule that has been designed so as to have at the N terminal a single chain antibody (scFv) in which a light chain and a heavy chain of an antibody variable region of an antibody that recognizes a molecule present on the cell surface of a cancer cell are linked in tandem, and to have at the C terminal a CD3ζ chain among molecules constituting a T cell receptor (TCR)/CD3 complex. This chimeric antigen receptor recognizes a specific antigen via the scFv region, then causing activation of a T cell via the CD3ζ chain. In order to enhance the activation of a T cell, one or more costimulators (e.g. CD28, 4-1BB, ICOS, etc.) may be incorporated between the scFv and the ζ chain. In the present invention, a CAR may be prepared using the TCR-like antibody of the present embodiment (including an antibody molecule designed from the TCR-like antibody or a fragment thereof) as the scFv. Since a CAR that recognizes a complex of a tumor antigen-derived peptide and an MHC can recognize a cancer cell that is presenting a tumor antigen peptide that can be targeted by a CTL, a dendritic cell that has phagocytized a cancer cell and is presenting a tumor antigen peptide on an MHC class I, etc., the genetically modified T cell into which the CAR has been introduced is useful as a preventive and/or therapeutic agent for a cancer that is specific to the tumor antigen, in the same way as for the artificial CTL. Therefore, the present invention also relates to a preventive and/or therapeutic agent for a cancer containing a genetically modified T cell or an artificial CTL into which has been introduced a CAR that recognizes a complex of the tumor antigen-derived peptide of the present invention and an MHC.

<11> Tumor Detection Method (Test Method, Diagnostic Method)

The present invention provides a tumor detection method (test method, diagnostic method) utilizing the CTL-detecting agent or the tumor cell-detecting agent (the tumor-detecting agent) of the present invention, which are described above.

The detection method (diagnostic method) of the present invention using the CTL-detecting agent of the present invention typically involves harvesting blood from a test subject or harvesting part of the test for which a tissue tumor is suspected by means of a biopsy, etc., and detecting/measuring the amount of CTLS that recognize a complex of an HLA antigen and a PVT1-, SUV39H2-, ZNF724P-, SNRNP40- or DYRK4-derived tumor antigen peptide contained therein by means of the CTL-detecting agent of the present invention, thus detecting, testing, or diagnosing the presence or absence or the extent of a PVT1-, SUV39H2-, ZNF724P-, SNRNP40-, or DYRK4-positive cancer (tumor) such as colon cancer, lung cancer, breast cancer, myeloma, oral cancer, pancreatic cancer, skin cancer, or prostate cancer.

The detection method (test method, diagnostic method) of the present invention using the tumor-detecting agent of the present invention typically involves detecting, testing, or diagnosing the presence or absence or the extent of a PVT1-, SUV39H2-, ZNF724P-, SNRNP40-, or DYRK4-positive cancer (tumor) such as colon cancer, lung cancer, breast cancer, myeloma, oral cancer, pancreatic cancer, skin cancer, or prostate cancer by harvesting blood from a test subject or harvesting by means of biopsy, etc. part of the test tissue for which a tumor is suspected, and detecting/measuring the amount of PVT1, SUV39H2, ZNF724P, SNRNP40, or DYRK4 expression product contained therein using the tumor-detecting agent of the present invention.

The detection method (test method, diagnostic method) of the present invention using the tumor-detecting agent of the present invention typically involves harvesting blood from a test subject or harvesting part of the test tissue for which a tumor is suspected by means a of biopsy, etc., and detecting/measuring the amount of cells presenting a complex of an HLA antigen and a PVT1-, SUV39H2-, ZNF724P-, SNRNP40- or DYRK4-derived tumor antigen peptide contained therein by means of the tumor-detecting agent of the present invention, thus detecting, testing, or diagnosing the presence or absence or the extent of a PVT1-, SUV39H2-, ZNF724P-, SNRNP40-, or DYRK4-positive cancer (tumor) such as colon cancer, lung cancer, breast cancer, myeloma, oral cancer, pancreatic cancer, skin cancer, or prostate cancer.

For example, the detection (test, diagnostic) method of the present invention can detect (test, diagnose) the presence or absence or the extent of improvement of a tumor when a therapeutic drug is administered to a patient having a tumor in order to improve the tumor. Furthermore, the detection (test, diagnostic) method of the present invention may be applied to the selection of a patient that is the subject of therapy to whom a medicament containing the peptide or the polynucleotide of the present invention as an active ingredient can be applied effectively, and to the prediction, assessment, etc. of the therapeutic effect of the medicament. Moreover, in an embodiment in which the tumor-detecting agent of the present invention is used, it is possible to detect a cancer cell presenting a tumor antigen peptide that can be actually targeted by a CTL induced within the living body of a patient by administering a cancer vaccine containing the peptide of the present invention as an active ingredient.

A specific embodiment of the detection (test) method of the present invention using the CTL-detecting agent of the present invention includes steps (a) and (b), and optionally step (c), as follows:

(a) a step of bringing a biological sample obtained from a test subject into contact with the CTL-detecting agent of the present invention, (b) a step of measuring the amount of CTLs that recognize a complex of an HLA antigen and a PVT1-, SUV39H2-, ZNF724P-, SNRNP40- or DYRK4-derived antigen peptide in the biological sample using the amount of cells to which the CTL-detecting agent binds as an indicator, and (c) a step of determining the presence of a cancer based on the result of (b).

A specific embodiment of the diagnostic method of the present invention using the CTL-detecting agent of the present invention includes steps (a), (b), and (c) above.

A specific embodiment of the detection (test) method of the present invention using the tumor cell-detecting agent of the present invention includes steps (d) and (e), and optionally step (f), as follows:

(d) a step of bringing a biological sample obtained from a test subject into contact with the tumor cell-detecting agent of the present invention, (e) a step of measuring the amount of PVT1, SUV39H2, ZNF724P, SNRNP40, or DYRK4 expression product in the biological sample, and (f) a step of determining the presence of a cancer based on the result of (e).

A specific embodiment of the diagnostic method of the present invention using the tumor cell-detecting agent of the present invention includes steps (d), (e), and (f) above.

An embodiment of the method for detecting a tumor cell using the tumor cell-detecting agent of the present invention includes steps (d) and (e) and step (f') below instead of (f):

(f') a step of determining the presence or absence of a tumor cell in a biological sample based on the result of (e).

Examples of the biological sample used here include a sample prepared from biological tissue (a tissue for which the presence of cancer cells is suspected, surrounding tissue thereof or blood etc.) of a test subject. Specific examples include a sample containing tissue cells harvested from the tissue.

A specific embodiment of the detection (test) method of the present invention using the tumor-detecting agent of the present invention includes steps (g) and (h), and optionally step (i), as follows:

(g) a step of bringing a biological sample obtained from a test subject into contact with the tumor-detecting agent of the present invention, (h) a step of measuring the amount of cells that present a complex of an HLA antigen and a PVT1-, SUV39H2-, ZNF724P-, SNRNP40-, or DYRK4-derived tumor antigen peptide in the biological sample using the amount of cells to which the tumor-detecting agent binds as an indicator, and (i) a step of determining the presence of a cancer based on the result of (h).

A specific embodiment of the diagnostic method of the present invention using the tumor-detecting agent of the present invention includes steps (g), (h), and (i) above.

Examples of the biological sample used here include a sample prepared from biological tissue (a tissue for which the presence of cancer cells is suspected, surrounding tissue thereof or blood etc.) of a test subject. Specific examples include a sample containing tissue cells harvested from the tissue.

One embodiment of the detection method (test method, diagnostic method) of the present invention using the CTL-detecting agent of the present invention is carried out by detecting a CTL specific to the peptide of the present in a biological sample and measuring the amount thereof. Specifically, a tetramer (HLA tetramer) of a complex of a fluorescently-labeled HLA antigen and the peptide of the present invention is prepared in accordance with a method described in the literature (Science, 274: p. 94, 1996, this publication forming part of the present application by reference), and this can be used for quantitatively determining by means of a flow cytometer the amount of antigen peptide-specific CTLs in peripheral blood lymphocytes of a patient for whom a cancer is suspected.

The prediction, assessment, determination, or diagnosis of the presence or absence of a tumor may be carried out by, for example, measuring the amount of CTLs specific to the peptide of the present invention in the blood or test tissue for which a tumor is suspected of a test subject or the amount of cells presenting the peptide of the present invention. In this process, in some cases, the level of PVT1, SUV39H2, ZNF724P, SNRNP40, or DYRK4 gene expression, the level of the peptide of the present invention, or the level of CTLs, etc. in the corresponding normal tissue may be used as a reference value, and this reference value may be compared with the level in the sample obtained from the test subject, the difference between the two being assessed.

The comparison of the levels between the test tissue of the test subject and the corresponding normal tissue may be carried out by measuring the biological sample of the test subject and a biological sample of a healthy subject in parallel. When it is not carried out in parallel, the average value or the statistical median of the amounts of CTLs specific the peptide of the present invention or the amounts of cells presenting the peptide of the present invention obtained using a plurality (at least two, preferably at least three, and more preferably at least five) of normal tissue pieces under uniform measurement conditions may be used in the comparison as the value for a healthy subject, that is, a reference value.

A determination of whether or not a test subject has a cancer may be carried out using as an indicator, for example, the amount of CTLs specific to the peptide of the present invention in tissue of the test subject or the cells presenting the peptide of the present invention being for example at least twice the level thereof in a healthy subject, and preferably at least three times.

Furthermore, in a test subject to which the peptide or the polynucleotide of the present invention is administered, it is also possible by measuring the amount of CTLs specific to the peptide of the present invention to assess whether or not CTLs have actually been induced. For example, it is possible to assess whether the therapy with the peptide or the polynucleotide of the present invention is effective by using as an indicator the amount of CTLs specific to the peptide of the present invention in the tissue of the test subject being for example at least twice the level thereof of a healthy subject, and preferably at least three times.

<12> Preventive and/or Therapeutic Method for Cancer

The present invention also relates to a method for the prevention and/or therapy of a cancer in a subject, the method including a step of administering an effective amount of an active ingredient selected from the group consisting of the peptide, the polynucleotide, the CTL, the antigen-presenting cell, the TCR-like antibody, the artificial CTL, and the genetically modified T cell of the present invention to a subject requiring same.

The 'subject' in the present invention may be any biological individual as long as it is a biological individual who can suffer from a cancer, but is preferably a human or a non-human mammalian individual (e.g. a rodent such as a mouse, a rat, a guinea pig, or a hamster, a primate such as a chimpanzee, an artiodactyl such as a cow, a goat, or a sheep, a perissodactyl such as a horse, and a rabbit, a dog, a cat, etc.), and more preferably a human individual. In the present invention, the subject may be healthy or may have any disease, but when the prevention and/or therapy of a cancer is intended, it typically means a subject having a cancer or having a risk thereof. In one embodiment of the present invention, the subject is HLA-A24-positive. In one embodiment of the present invention, the subject has a PVT1-, SUV39H2-, ZNF724P-, SNRNP40-, or DYRK4-positive cancer or has a risk thereof. In one embodiment of the present invention, the subject is HLA-A24-positive and has a PVT1-, SUV39H2-, ZNF724P-, SNRNP40-, or DYRK4-positive cancer or has a risk thereof.

With regard to the peptide, the polynucleotide, the CTL, the antigen-presenting cell, the TCR-like antibody, the artificial CTL, and the genetically modified T cell of the present invention used in the preventive/therapeutic method of the present invention, any one described in the present specification can be cited. The effective amount referred to in the present invention is an amount that for example reduces the symptoms of a cancer or delays or halts the progress thereof, and is preferably an amount that suppresses or cures a cancer. Furthermore, it is preferably an amount that does not cause an adverse effect that exceeds the benefit obtained by administration. Such an amount may be determined as appropriate by means of an in vitro test using cultured cells, etc. or a test in a model animal such as a mouse or a rat, and such test methods are well known to a person skilled in the art. The specific dose of an active ingredient may be determined while taking into consideration various conditions related to a subject same, requiring for example, the seriousness of symptoms, the general health state, age, and body weight of the subject, the sex of the subject, diet, timing and frequency of administration, concomitant medication, response to therapy, dosage form, compliance with therapy, etc.

In the case of for example the peptide of the present invention, the specific dose is usually 0.0001 mg to 1000 mg, preferably 0.001 mg to 1000 mg, and more preferably 0.1 mg to 10 mg, and this is preferably administered once in a few days to a few months. Furthermore, in the case of the polynucleotide of the present invention, it is usually 0.0001 mg to 100 mg, and preferably 0.001 mg to 10 mg, and this is preferably administered once in a few days to a few months. In the case of the TCR-like antibody of the present invention, it is usually 0.0001 mg to 2000 mg, and preferably 0.001 mg to 2000 mg, and this is preferably administered once in 1 week to 4 weeks. In the case of the genetically modified T cell or artificial CTL of the present invention, it is usually $1 \times 10^4$ to $1 \times 10^8$, and preferably $1 \times 10^5$ to $1 \times 10^7$, and this is preferably administered once in 1 day to 4 weeks. As an administration method, any known appropriate administration method such as intradermal administration, subcutaneous administration, intramuscular administration, or intravenous administration may be used. It is also possible to use an in vivo method in which the peptide or the nucleotide of the present invention is directly administered into the body as well as an ex vivo method in which a specific type of cell is collected from a person, CTLs or antigen-presenting cells are induced in vitro using the peptide or the polynucleotide of the present invention, and these cells are subsequently returned into the body.

One embodiment of the preventive/therapeutic method of the present invention further includes, prior to the administration step, a step of selecting a subject who is HLA-A24-positive as a subject for the prevention/therapy. This embodiment of the present invention may further include, prior to the selection step, a step of determining the HLA type of a subject. Determination of the HLA type of a subject may be carried out by any known method. Furthermore, one embodiment of the preventive/therapeutic method of the present invention further includes, prior to the administration step, a step of selecting a subject who has a PVT1-, SUV39H2-, ZNF724P-, SNRNP40-, or DYRK4-positive cancer as a subject for the prevention/therapy. This embodiment of the present invention may further include, prior to the selection step, a step of detecting a PVT1-, SUV39H2-, ZNF724P-, SNRNP40-, or DYRK4-positive cancer in a subject. Detection of a PVT1-, SUV39H2-, ZNF724P-, SNRNP40-, or DYRK4-positive cancer in a subject may be carried out by the tumor detection method described in <11> above. One embodiment of the preventive/therapeutic method of the present invention further includes, prior to the administration step, a step of selecting a subject who is HLA-A24-positive and has a PVT1-, SUV39H2-, ZNF724P-, SNRNP40-, or DYRK4-positive cancer as a subject for the prevention/therapy. This embodiment of the present invention may further include, prior to the selection step, a step of determining the HLA type of a subject and a step of detecting a PVT1-, SUV39H2-, ZNF724P-, SNRNP40-, or DYRK4-positive cancer in a subject.

<13> Method for Screening Cancer Therapy Drugs Targeting Tumor Cells

In an embodiment in which the tumor cell-detecting agent of the present invention is used, the amount of PVT1, SUV39H2, ZNF724P, SNRNP40, or DYRK4 expression product expressed in a detection target expected to have a positive can be correlation with the amount of tumor cells in the detection target. Therefore, it is possible by comparing the amounts of PVT1, SUV39H2, ZNF724P, SNRNP40, or DYRK4 expression product expressed before and after administering a candidate compound for a cancer therapy drug to a detection target to determine whether or not the candidate compound administered is useful as a cancer therapy drug targeting tumor cells.

The screening method of the present invention includes steps (I) and (II), and optionally (III):

(I) a step of measuring a detected amount A of an expression product of the PVT1, SUV39H2, ZNF724P, SNRNP40, or DYRK4 gene in a subject before administering a candidate compound for a cancer therapy drug to the subject, (II) a step of measuring a detected amount B of an expression product of said gene in the subject after administering the candidate compound to the subject cell population, and (III) a step of determination of the candidate compound as a cancer therapy drug candidate with cancer stem cells as a target when the detected amounts A and B are compared and the detected amount A is significantly larger than B.

A specific embodiment of the screening method of the present invention includes steps (I) to (III) above. The step of measuring the amount detected in step (I) and (II) includes steps (d) and (e) in the detection (test, diagnosis) method.

<14> Polynucleotide for Suppressing Gene Expression

As described above, it has been found for the first time that a gene selected from the group consisting of PVT1, SUV39H2, ZNF724P, SNRNP40, and DYRK4 is a cancer testis antigen that is not expressed in normal cells other than the testis but is expressed in a tumor cell. This suggests that expression these genes is involved in the malignant transformation of a cell, and it can therefore be expected that suppressing the expression of these genes will enable the cancer to be treated.

That is, one embodiment of the present invention relates to a gene expression suppressing agent that suppresses the expression of a gene selected from the group consisting of PVT1, SUV39H2, ZNF724P, SNRNP40, and DYRK4.

The method for selectively suppressing the expression of a specific gene in a cell is not particularly limited, and examples thereof include an antisense RNA method, an RNA interference (RNAi) method, a CRISPR-Cas method, a ZFN method, and a TALEN method. Among them, from the viewpoint of bioavailability, low off-target effects, etc., an antisense RNA method and an RNAi method are preferable, and an RNAi method is more preferable.

Therefore, in a preferred embodiment of the present invention, the gene expression suppressing agent is an antisense oligonucleotide toward a gene selected from the group consisting of PVT1, SUV39H2, ZNF724P, SNRNP40, and DYRK4. The 'antisense oligonucleotide' toward a given gene referred to in the present invention means an oligonucleotide that can suppress the expression of said gene by hybridizing with an mRNA that is an expression product of said gene, and this may be any nucleic acid such as DNA or RNA. Such an oligonucleotide is typically an oligonucleotide having a sequence complementary to part of the sequence of mRNA of said gene. The term 'complementary to' referred to here means that a given nucleic acid can form hydrogen bonding with another nucleic acid sequence, and the term 'sequence complementary to (part of) a specific sequence' means a sequence that has complementarity to a degree that enables it to hybridize with a nucleotide having said sequence in the intracellular environment. Therefore, not all of the sequence needs to be complementary (i.e. completely complementary).

The antisense oligonucleotide of the present invention typically has a length of about 15 to 30 nucleotides. It may be subjected to a modification known in the present technical field for the purpose of improving the stability or the activity in suppressing expression in a living body, reducing off-target effects, etc.

Furthermore, in a preferred embodiment of the present invention, the gene expression suppressing agent is an siRNA for a gene selected from the group consisting of PVT1, SUV39H2, ZNF724P, SNRNP40, and DYRK4. An 'siRNA' for a given gene referred to in the present invention means a double strand RNA that can inhibit the expression of said gene; said double strand RNA has a sense region and an antisense region, the antisense region is complementary to an mRNA sequence of the specific gene, and the sense region is complementary to the antisense region sequence. The sense region and the antisense region of the siRNA of the present invention each have a length of about 15 to 30 nucleotides and preferably have a length of 19 to 27 nucleotides. Furthermore, the sense region and the antisense region may form a double strand structure from two strands, that is, a sense strand and an antisense strand. Moreover, the sense region and the antisense region may be linked to form one nucleotide chain, and in this case one strand of RNA is folded into a hairpin shape, and the sense region and the antisense region form a double strand structure.

In the present technical field, a method for improving the expression suppressing effect of an siRNA, a method of improving bioavailability, or a method of reducing off-target effects is known. The siRNA of the present invention may appropriately be subjected to known modification or alteration for improving the function as an siRNA.

The polynucleotide may easily be synthesized by a known method in the present technical field, for example, by using a commercial DNA synthesizer.

In another aspect, the present invention provides a pharmaceutical composition containing the antisense oligonucleotide and/or the siRNA. As another component that can be contained in the pharmaceutical composition of the present embodiment, for example, a pharmaceutically acceptable carrier, a diluent, an excipient, etc. can be cited, and it is particularly preferable for it to contain a pharmaceutically acceptable carrier. Examples of the pharmaceutically acceptable carrier include, but are not limited to, a liposome and a hydrophilic polymer.

As described above, it can be expected that it will be possible to treat a cancer by suppressing the expression of a gene selected from the group consisting of PVT1, SUV39H2, ZNF724P, SNRNP40, and DYRK4. Therefore, the pharmaceutical composition containing the polynucleotide of the present embodiment may be used as an agent for the prevention and/or therapy of a cancer.

In another aspect, the present invention relates to a method for the prevention and/or therapy of a cancer, the method comprising suppressing the expression of a gene selected from the group consisting of PVT1, SUV39H2, ZNF724P, SNRNP40, and DYRK4. This method may be carried out in accordance with the method described in <12> above except that the active ingredient to be administered is a gene expression suppressing agent that suppresses the expression of a gene selected from the group consisting of PVT1, SUV39H2, ZNF724P, SNRNP40, and DYRK4, and is preferably an antisense oligonucleotide or siRNA that suppresses the expression of a gene selected from the group consisting of PVT1, SUV39H2, ZNF724P, SNRNP40, and DYRK4.

That is, the method can be said to be a method for the prevention and/or therapy of a cancer, the method comprising a step of administering an effective amount of expression suppressing agent for a gene selected from the group consisting of PVT1, SUV39H2, ZNF724P, SNRNP40, and DYRK4 to a subject who needs it. The subject may be healthy or may have any disease, but when the prevention and/or therapy of a cancer is intended, it typically means a subject having a cancer or having a risk thereof. Therefore, the subject has a PVT1-, SUV39H2-, ZNF724P-, SNRNP40-, or DYRK4-positive cancer, or has a risk of having it.

Furthermore, one embodiment of the preventive/therapeutic method of the present invention further includes, prior to the administration step, a step of selecting a subject who has a PVT1-, SUV39H2-, ZNF724P-, SNRNP40-, or DYRK4-positive cancer as a subject for the prevention/therapy. When selecting a subject, a method for detecting a PVT1-, SUV39H2-, ZNF724P-, SNRNP40-, or DYRK4-positive cancer may be applied to the subject in <11> above.

The effective amount referred to in the present embodiment is an amount that for example reduces the symptoms of a cancer or delays or halts the progress thereof, and is preferably an amount that suppresses or cures a cancer. Furthermore, it is preferably an amount that does not cause an adverse effect that exceeds the benefit obtained by administration. Such an amount may be determined as appropriate by means of an in vitro test using cultured cells, etc. or a test in a model animal such as a mouse or a rat, and such test methods are well known to a person skilled in the art. The specific dose of an active ingredient may be determined while taking into consideration various conditions related to a subject requiring same, for example, the seriousness of symptoms, the general health state, age, and body weight of the subject, the sex of the subject, diet, timing and frequency of administration, concomitant medication, response to therapy, dosage form, compliance with therapy, etc.

All patents, applications, and other publications referred to in the present specification are incorporated herein by reference in their entirety.

The present invention is specifically explained below by reference to Examples, but the present invention should not be construed as being limited by these Examples.

EXAMPLES

Example 1. Identification of Natural Peptide Presented on HLA-A24

(1) Ascertainment of Cell Surface HLA-A24 Molecule

Localization of HLA-A24 molecules present on the cell surface was researched using SW480, HCT-116, HCT-15/β2m, and Colo320, which are human colon carcinoma cell lines, LHK2, which is a lung adenocarcinoma cell line, and Sq-1, which is a lung squamous carcinoma.

The cultured cancer cells were treated with 0.25% trypsin-EDTA (Gibco), washed with ice-cooled PBS, and poured into a round bottom 96 well plate (Corning) to give about $2 \times 10^5$ cells/well. The cells were centrifuged at 380 g for 5 minutes, and incubated on ice for 1 hour together with a culture supernatant of anti-HLA-A24 monoclonal antibody-producing mouse hybridoma C7709A2 (donated by Dr P. G. Coulie (de Duve Institute, Brussel)) or anti-pan HLA class I antibody-producing mouse hybridoma W6/32. The cells were washed with ice-cooled PBS and then incubated on ice for 30 minutes together with FITC-conjugated goat anti-mouse IgG antibody. The cells were again washed with ice-cooled PBS, then resuspended in 1% formaldehyde-containing PBS, and subjected to analysis with a BD FACS Calibur system (BD Biosciences, Mountain View, CA), thus measuring the fluorescence intensity, which is proportional to the amount of HLA-A24 molecules.

The results are shown in FIG. 1. It was observed that among the six types of cell lines used (SW480, HCT-116, HCT-15/β2m, Colo320, LHK2, and Sq-1), five types, that is, SW480, HCT-15/62m, Colo320, LHK2, and Sq-1, which are genetically HLA-A*2402, gave the same level of fluorescence intensity for the C7709A2 antibody as for the W6/32 antibody. This means that a complex between HLA-A24 and a natural peptide on the cell surface was selectively detected by C7709A2.

(2) Isolation of Peptide

Isolation of a complex of HLA-A24 and a natural peptide localized on the cancer cell surface was carried out in accordance with a method described in Purcell et al., Methods Mol Biol. 2004, 251, 291-306 and Escobar et al., J. Immunol, 2008, 181:4874-4882. In brief, a culture supernatant of anti-HLA-A24 monoclonal antibody-producing mouse hybridoma C7709A2 (donated by Dr P. G. Coulie (de Duve Institute, Brussel)) was collected and concentrated to about 1/40 of the volume by reverse osmosis against PEG-20,000 (WAKO chemicals), and about 40 mL of the concentrate (adjusted to a pH of about 7.2 to 7.4) was added to about 3 mL of washed protein A-Sepharose beads (GE Healthcare) and incubated at 4° C. overnight with shaking.

Subsequently, the beads were washed with 0.1M boric acid buffer (pH8.2) and 0.2M triethanolamine (pH8.2). A protein A-binding antibody was linked by covalent bonding to the beads by resuspending in a solution of 20 volumes of 20 mM dimethyl pimelimidate (DMP) dihydrochloride (Sigma) in 0.2M triethanolamine (pH 8.3). A coupling reaction proceeded in a Rotamix at room temperature for 1 to 1.5 hours. Free imidic acid groups remaining in the DMP were quenched by incubating the Sepharose beads together with 10 volumes of 20 to 50 mM monoethanolamine solution in a Rotamix at room temperature for 2 hours. Subsequently, the beads were washed with a 0.1M boric acid buffer and stored at 4° C. with 0.02% sodium azide.

The cells used were from the cell line used in (1) above. The cells were lysed in an ice-cooled buffer containing 0.5% Nonidet P-40, 50 mM Tris-HCl, and 150 mM NaCl and protease inhibitor (Roche). The cell lysate was clarified by centrifugations in series at 2,000 g-10 minutes, 38,000 g-30 minutes, and 100,000 g-90 minutes at 4° C. After the last centrifugation, the supernatant was collected and subjected to passage through a 0.5 mL protein A-Sepharose beads slurry in a Poly-Prep Chromatography Column (Bio-Rad), thus removing all molecules nonspecifically binding to the protein A.

The unpurified lysate thus obtained was mixed with protein A-Sepharose beads having covalently bonded thereto 1 mL of anti-HLA-A24 monoclonal antibody (C7709A2) prepared above and gently Rotamixed at 4° C. overnight. The beads were washed in sequence with four ice-cooled buffers (buffer 1: 0.005% Nonidet P-40, 50 mM Tris-HCl, pH 8.0, 150 mM NaCl, 5 mM ethylenediamine tetraacetic acid (EDTA) and protease inhibitor, buffer 2: 50 mM Tris-HCl, pH 8.0 and 150 mM NaCl, buffer 3: 50 mM Tris-HCl, pH 8.0 and 450 mM NaCl, buffer 4: 50 mM Tris-HCl, pH 8.0). Finally, a complex between the HLA molecule and peptide was eluted with 6 mL of 10% acetic acid. Subsequently, the HLA molecule and the peptide were separated by ultrafiltration using 3 kDa cutoff filter Amicon Ultra-15 Centrifugal Filter Units (Millipore). The flow-through fraction up to 5.5 mL thus obtained was concentrated to a few microliters by a SpeedVac, dissolved again in 0.1% formic acid as a solvent, and subjected to a nanoflow HLPC system linked to an MALDI spotting device.

(2) Identification of Peptide

The peptide was separated on a HiQsilC18W-3 column (100 μm ID×100 mm; KYA Technologies, Tokyo, Japan) in a DiNa system (KYA Technologies) linked to a MALDI spotting device. 0.1% Trifluoroacetic acid (TFA) was used as elution solvent A, and 0.1% trifluoroacetic acid in 70% acetonitrile was used as elution solvent B. The concentration gradient was set so that solvent B went from 5% to 50% over 80 minutes, and the flow rate was 300 nL/min. The separated peptide was spotted on an Opti-TOF™ 384 Well Insert (123×81 mm) stainless MALDI plate (AB Sciex, Foster City, CA) in a DiNa MaP MALDI spotting system. 150 nL of a peptide fraction was collected every 30 seconds and overlaid mg/mL α-cyano-4-hydroxycinnamic acid (CHCA; Sigma, Tokyo, Japan) and 80 μg/mL di-ammonium hydrogen citrate in 70% ACN/0.1% TFA. Mass analysis was carried out using a 4800 Plus MALDI-TOF/TOF Analyzer (AB Sciex) and 4000 Series Explorer software (ver. 3.5.3) (AB Sciex). In order to calibrate the mass accuracy, a trypsinized BSA standard (KYA Technology) and 6-peptide mixture (AB Sciex) were used.

Precursor ion scanning was carried out in the range of 600 to 3500 m/z, and precursor ions up to 100 ions having an S/N threshold value of 10 or greater resulting from was fragmentation were selected (TOP100 algorithm). MS/MS obtained using air as a collision gas with a collision energy of 1 kV. Identification of a peptide from the obtained data was carried out using a Paragon search algorithm, which has been adopted by ProteinPilot 3.0 software (AB Sciex), through the human International Protein Index (IPI) database (ipi.HUMAN.v3.71.fasta, containing 86739 types of protein sequences, and ipi.HUMAN.v3.87.fasta, containing 91444 types of protein sequences) UniProt Knowledge Base (UniProtKB_HUMAN.fasta, containing 88993 types of protein sequence as of June 2014).

For the study, the following settings were selected: sample type-identification; Cys. alkylation-none; digestion-none; instrument-4800; species-*Homo sapiens*; ID Focus-no focus/focus on amino acid substitutions; search effort-thorough. Raw data for peptide identification (ProteinPilot's.group files) were moved to an Excel file format (Microsoft), matching between an MS/MS ion signal and an amino acid sequence for which the spectrum was identified was studied manually, and those determined to be false positives were removed from the list.

The results are shown in FIG. 2. The natural peptide was isolated from the complex obtained and the sequence thereof was determined, and from the results for all of the five types of cell lines the majority were natural peptides having a length of 9 amino acids. When the amino acid residue distribution at each amino acid position was examined, the majority were peptides having tyrosine for the second amino acid from the N terminal and/or phenylalanine for the amino acid at the C terminal (FIG. 2). This coincides with a binding motif of HLA-A24.

When the parent proteins of 384 natural peptides whose sequence was determined by MS/MS were further examined, most (304 types) thereof were the only ones derived from their parent proteins. Among the identified parent proteins, 30 proteins gave two natural peptides, 5 proteins gave three natural peptides, and 1 protein gave five natural peptides.

Example 2. HLA-A24 Binding Assay (1) Synthesis of Peptide

The natural peptides identified in Example 1 were produced by synthesis (PH Japan Co. Ltd., Hiroshima). A peptide having a purity of 70% or greater was used for the binding assay. As a negative control for HLA-A24 binding, synthetic peptide GK12 (SEQ ID No: 6) was used.

(2) Binding Assay

T2-A24 cells, which are HLA-A24-expressing T2 cells, were preincubated in a $CO_2$ incubator at 27° C. overnight. The cells collected were resuspended in Opti-MEM and plated on a round bottom 96 well plate (Corning) with about $1 \times 10^5$ cells/200 µL per well. A subject peptide was added at concentrations of 0.33 µM, 1 M, and 10 µM, and incubation was carried out in a $CO_2$ incubator at 27° C. for 3 hours and subsequently at 37° C. for 2.5 hours. Subsequently, the cells were subjected to centrifugation (380 g, 5 minutes) as they were on the plate, resuspended in 100 µL of a C7709A2 monoclonal antibody-producing hybridoma culture supernatant, and incubated on ice for 45 to 60 minutes. The cells were washed with ice-cooled PBS and then incubated together with an FITC-conjugated goat anti-mouse IgG antibody (KPL, Gaithersburg, MD) on ice for 30 minutes. The cells were washed with ice-cooled PBS as they were on the plate, then resuspended in 1% formaldehyde and PBS, and analyzed by a FACScan (BD Biosciences, Mountain View, CA), and the mean fluorescence intensity (MFI) shift (fluorescence increase as a result of stabilization by binding peptide) due to an increase in the amount of stable HLA-A24 molecules was thus measured. A cell treated with nonbinding peptide GK12 (concentration 0 to 10 µM) has a constant MFI and it was used as a negative control.

The MFI shift (ΔMFI) for a peptide concentration of 1 µM was measured for 26 types of randomly selected peptides of the natural peptides obtained in Example 1 above. A score was also calculated for these peptides using NetMHC3.4, and correlation with ΔMFI was investigated. The results are shown in FIG. 3. It was found that ΔMFI and NetMHC score had a linear correlation with a coefficient of determination of $R^2=0.6$. It has been found that when the NetMHC score is larger than a threshold value of 0.15 (corresponding to a ΔMFI of 17) it can be surmised to be a binding peptide. As a result, it has been found that 273 types of peptides of the 384 types of identified natural peptides can be surmised to be binding peptides (i.e. NetMHC>0.15) (data not shown).

Example 3. Identification of Tumor-Specific Gene (1) Ascertainment of Expression of Parent Gene in Normal Tissue In order to ascertain gene expression in each normal tissue, a human cDNA panel standardized by housekeeping gene (Human MTC Panels I and II, Clontech) was used. Total RNA of each cancer cell line was prepared using an RNeasy Mini Kit (Qiagen), and cDNA was prepared using oligo (dT) primer and SuperScript III reverse transcriptase (Invitrogen).

Expression of a gene (parent gene) encoding a parent protein of 273 types of peptides surmised to be binding peptides in Example 2 was ascertained by PCR using the cDNA library prepared above. A primer set was designed so that a region encoding the natural peptide was included and the PCR product had a length of about 200 to 400 base pairs. PCR was carried out with a volume of 20 µL containing DreamTaqDNA polymerase, 10× DreamTaq buffer (Thermo Scientific), 2 mM dNTP mixture, 0.25 µM forward and reverse primers, and the corresponding cDNA template. The PCR cycles were carried out under the following conditions:

TABLE 1

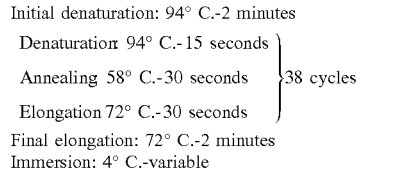

| Initial denaturation: 94° C.-2 minutes |
| Denaturation: 94° C.-15 seconds ⎫ |
| Annealing 58° C.-30 seconds ⎬ 38 cycles |
| Elongation 72° C.-30 seconds ⎭ |
| Final elongation: 72° C.-2 minutes |
| Immersion: 4° C.-variable |

The PCR products thus obtained were subjected to electrophoresis with 1.5% agarose gel, visualized with ethidium bromide, and examined under UV light.

(2) Identification of Cancer Testis Antigen

Among genes known as cancer antigens, there are genes whose expression has hardly ever been substantiated in normal tissue cells. Since the expression of such genes is often substantiated only in the testis, they are called 'cancer testis antigens'. From the results of (1) above, genes that were surmised to be cancer testis antigens were selected. From the results, 6 types of genes, that is, PVT1, SUV39H2, ZNF724P, SNRNP40, DYRK4, and TOPK/CT84 were surmised to be cancer testis antigens. Among them, it has already been reported that TOPK/CT84 is a cancer testis antigen and a peptide derived from said gene is presented as an antigen on a cancer cell (International Patent Application WO2013/061594).

Example 4. Evaluation of Natural Antigen Peptide

An evaluation test as a natural antigen peptide was carried out for each natural peptide whose parent gene is surmised as the cancer testis antigen gene in Example 3.

PVT1: HWNDTRPAHF (SEQ ID No: 1)
SUV39H2: RYGNVSHF (SEQ ID No: 2)
ZNF724P: KYVKDFHKF (SEQ ID No: 3)
SNRNP40: IFQGNVHNF (SEQ ID No: 4)
DYRK4: VYTYIQSRF (SEQ ID No: 5)

Expression analysis of the above genes employed the primer sets listed in the table below.

TABLE 2

| Gene name | | Sequence |
|---|---|---|
| PVT1 | Fw | ctgtgacctgtggagacacg (SEQ ID No: 7) |
| | Rv | cacagcctcccttaaaacca (SEQ ID No: 8) |
| SUV39H2 | Fw | cgaactagcaatggacgtgg (SEQ ID No: 9) |
| | Rv | caatgctattcggggaagac (SEQ ID No: 10) |
| ZNF724P | Fw | ccaagaccttcggccaga (SEQ ID No: 11) |
| | Rv | tgagaaagggttgaggacac (SEQ ID No: 12) |
| SNRNP40 | Fw | ataaaaccgtggctgtgtgg (SEQ ID No: 13) |
| | Rv | cactgaatctgcatggcctc (SEQ ID No: 14) |
| DYRK4 | Fw | ccaaggcagaggagaagtca (SEQ ID No: 15) |
| | Rv | ccttcccgattgtctccaga (SEQ ID No: 16) |

(1) PVT1 and Natural Peptide Derived Therefrom
The test results for PVT1 and the peptide of SEQ ID No: 1 are shown in FIG. 4. PVT1 has been known as an ncRNA, but the present inventors have suggested the possibility that it is expressed at the protein level at least in cancer cells.

Expression PVT1 at the mRNA level has not been substantiated in normal tissue cells other than the testis, and since the peptide of SEQ ID No: 1 derived from PVT1 showed high binding to HLA-A24, it can be expected that it will be useful as a target in immunotherapy. Furthermore, since said gene is specifically expressed in a cancer cell and there is a possibility of it being involved in the malignant transformation or survival of a cancer cell, an effect as a target for nucleic acid treatment by suppression of the expression, etc. can be anticipated.

(2) SUV39H2 and Natural Peptide Derived Therefrom
The test results for SUV39H2 and the peptide of SEQ ID No: 2 are shown in FIG. 5. Expression of SUV39H2 at the mRNA level has not been substantiated in normal tissue cells other than the testis, and since the peptide of SEQ ID No: 2 derived from SUV39H2 showed high binding to HLA-A24, it can be expected that it will be useful as a target in immunotherapy. Furthermore, since said gene is specifically expressed in a cancer cell and there is a possibility of it being involved in the malignant transformation or survival of a cancer cell, an effect as a target for nucleic acid treatment by suppression of the expression, etc. can be anticipated.

(3) ZNF724P and Natural Peptide Derived Therefrom
The test results for ZNF724P and the peptide of SEQ ID No: 3 are shown in FIG. 6. Expression of ZNF724P at the mRNA level has not been substantiated in normal tissue cells other than the testis, and since the peptide of SEQ ID No: 3 derived from ZNF724P showed high binding to HLA-A24, it can be expected that it will be useful as a target in immunotherapy. Furthermore, since said gene is specifically expressed in a cancer cell and there is a possibility of it being involved in the malignant transformation or survival of a cancer cell, an effect as a target for nucleic acid treatment by suppression of the expression, etc. can be anticipated.

(4) SNRNP40 and Natural Peptide Derived Therefrom
The test results for SNRNP40 and the peptide of SEQ ID No: 4 are shown in FIG. 7. Expression of SNRNP40 at the mRNA level has not been substantiated in normal tissue cells other than the testis, and since the peptide of SEQ ID No: 4 derived from SNRNP40 showed high binding to HLA-A24, it can be expected that it will be useful as a target in immunotherapy. Furthermore, since said gene is specifically expressed in a cancer cell and there is a possibility of it being involved in the malignant transformation or survival of a cancer cell, an effect as a target for nucleic acid treatment by suppression of the expression, etc. can be anticipated.

(5) DYRK4 and Natural Peptide Derived Therefrom
The test results for DYRK4 and the peptide of SEQ ID No: 5 are shown in FIG. 8. Expression of DYRK4 at the mRNA level has not been substantiated in normal tissue cells other than the testis, and since the peptide of SEQ ID No: 5 derived from DYRK4 showed high binding to HLA-A24, it can be expected that it will be useful as a target in immunotherapy. Furthermore, since said gene is specifically expressed in a cancer cell and there is a possibility of it being involved in the malignant transformation or survival of a cancer cell, an effect as a target for nucleic acid treatment by suppression of the expression, etc. can be anticipated.

Example 5. CTL Induction and Evaluation (1) CTL Induction
Peripheral blood was collected using a heparin-containing 50 ML syringe from HLA-A24-positive healthy controls who had given informed consent. The whole blood was layered in a 50 mL tube (Falcon) to which 13 mL of Lymphoprep (Nycomed) had been added, and subjected to centrifugation at 2000 rpm for 30 minutes. A PBMC layer precipitated on the Lymphoprep layer was recovered using a pipette and washed three times with PBS, thus giving human PBMC.

About 3×10⁷ cells/plate of the human PBMC separated above and 10 mL of Hepes-modified RPMI1640 medium (Sigma) containing 2-mercaptoethanol (final concentration 55 μM), L-glutamine (final concentration 2 mM), as antibiotics streptomycin (final concentration 100 μg/mL) and penicillin G (final concentration 100 U/mL), and 5% serum component were placed in each well of a 96 well round bottom micro test plate for cell culture (BECTON DIKINSON), and suspension cultured. PVT1-derived natural antigen peptide of SEQ ID No: 1 (hereinafter referred to as 'HF10') or SUV39H2-derived natural antigen peptide of SEQ ID No: 2 (hereinafter referred to as 'RF8') were added thereto at a concentration of 10 μg/mL. After culturing was carried out for 2 days, IL-2 was added at a final concentration of 50 U/mL, and culturing was carried out for a further 2 weeks.

20 μL of CD8-FITC antibody and 10 μL of a PE-labeled HF10/HLA-A24 tetramer reagent for the HF10 pulsed cells and a PE labeled RF8/HLA-A24 tetramer reagent for the RF8 pulsed cells were added to an appropriate amount of cultured cells, gently mixed, and allowed to stand at 4° C. for 30 minutes. After 1.5 mL of PBS was added and stirred, centrifugation was carried out at 3,000 rpm for 5 minutes, the supernatant was aspirated and discarded, the cells were resuspended in 400 μL of PBS, analysis was carried out by a flow cytometer within 24 hours, and the cell fraction with CD8 (+) and HLA-A24 tetramer (+) was sorted and proliferated, thus preparing a CD8+ T cell clone, which was used as a CTL.

FIG. 9 shows the result of analysis of the properties of each CTL by flow cytometry (tetramer assay) using an HLA-A24 tetramer reagent. All lines showed CD8 (+) and natural antigen peptide/HLA-A24 tetramer (+). Furthermore, the RF8 pulsed CTL was suggested to have low binding ability to an HIV/HLA-A24 tetramer and high specificity to the RF8/HLA-A24 tetramer.

(2) Interferon (IFN)-γ ELISPOT Assay

An experiment was carried out using a Human IFNγ ELISPOT set (BD). An ELISPOT plate was coated with anti-IFNγ antibodies, which had been diluted by 200 times, and allowed to stand at 4° C. overnight. The plate was cultured in 10% FCS-supplemented RPMI (Sigma-Aldrich) at room temperature for 2 hours and blocking was carried out, thus giving an ELISPOT plate.

T2-A24 cells (donated by Dr. Kuzushima, Aichi Cancer Center), which are of a cell line expressed by transferring the HLA-A2402 gene to human lymphoblastoid T2 cells, were pulsed with each peptide at a concentration of 20 μg/mL at room temperature for 1 hour. With regard to the peptide pulsed groups there were three groups, that is, [1] no peptide pulse, [2] HIV peptide pulse, and [3] HF10 or RF8 peptide pulse. PBS was added subsequent to the peptide pulse, and centrifugation was carried out at 1500 rpm for 5 minutes. A cell pellet was suspended to give $5 \times 10^5$ cells/mL, and an ELISPOT plate was plated with $5 \times 10^4$ cells per well. The CTLs prepared above were plated at $5 \times 10^4$ cells per well and cultured at 37° C. overnight.

The culture medium and the cells were removed from the ELISPOT plate that had been cultured overnight, and the ELISPOT plate was washed twice with Milli Q water and three times with wash buffer. Biotinylated detection antibody diluted by 250 times was added to each well, and culturing was carried out at room temperature for 2 hours. After washing three times with wash buffer, HRP-labeled streptavidin diluted by 100 times was added to each well, and culturing was carried out at room temperature for 1 hour. After washing three times with wash buffer and washing twice with PBS, a chromogenic reagent was added to each well, and a chromogenic reaction was carried out at room temperature for 15 to 30 minutes. After sufficient visible spot formation was detected, washing with Milli Q water was carried out, and the reaction was thus completed. A nitrocellulose film was dried and then subjected to detection and imaging by KS ELISPOT (ZEISS).

An ELISPOT assay was similarly carried out using cancer cells as the target cells instead of the peptide-pulsed T2-A24 cells. The cancer cells used were SW480 and colo320 large intestine cancer cells and Sq-1 lung cancer cells for CTL clones A10, E10, and H3, and SW480 large intestine cancer cells for CTL clone 11.

The results are shown in FIG. 10. A shows the result of an assay using CTL clones A10, E10 and H3 induced using HF10 peptide. All clones showed specific reactivity toward HF10-pulsed T2-A24 cells. Furthermore, in an assay using cancer cells, reactivity toward SW480 and colo320, for which PVT1 mRNA was detected in Example 4, was shown, but no reaction was observed for Sq-1, for which PVT1 mRNA was not detected. This indicates that SW480 and colo320 express a PVT1 protein and HF10 is presented as an antigen on the cell surface.

B shows the result of an assay using CTL clone 11 induced using an RF8 peptide. This also showed specific reactivity toward RF8-pulsed T2-A24 cells in the same way as for HF10. Furthermore, specific reactivity was also shown toward SW480 cells, which are cells from which RF8 was isolated, instead of the peptide pulsed cells. This indicates that SW480 presents RF8 on the cell surface as an antigen.

(3) LDH Killing Assay

Analysis of whether an RF8 peptide-specific CTL prepared above actually attacked cells expressing SUV39H2 was carried out by an LDH killing assay (TakaRa Bio). First, as the target cell (Target) that is the subject of attack by the RF8 peptide-specific CTL, peptide pulsed T2-A24 cells were prepared in the same way as for (2) above. The target cells were plated on a 96 well V-bottom plate (Corning) at $1 \times 10^4$ cells/well. The number of RF8 specific CTLs (Effector) was adjusted for each well so as to give an E/T ratio stated in FIG. 11 (that is, 3 times, 10 times, and 30 times the target cell), and mixed with the target cells plated on the 96 well plate. Subsequently, the 96 well plate was subjected to centrifugation at 1800 rpm for 10 minutes and allowed to stand in a $CO_2$ incubator at 37° C. for 4 hours to 12 hours. After the 96 well plate was subjected to centrifugation and the cells were precipitated, 100 μL of supernatant was moved to a flat bottom 96 well plate. 100 μL of a reaction solution containing diaphorase was added to each well and allowed to stand at room temperature for 30 minutes, and the absorbance at 490 nm was measured. If the cell is damaged, since this operation makes LDH, which is usually present within the cell membrane, be released outside the cell due to damage to the cell membrane, it becomes possible to asses cytotoxicity by measuring the amount of LDH in the culture solution as an absorbance. Whether the RF8 peptide-specific CTL recognizes and attacks target cell presenting an RF8 peptide was investigated using this method.

The same test was carried out using various types of cancer cell lines as the target cell. As the target cell, in addition to the SW480 large intestine cancer cell line, from which RF8 was isolated, the LHK2 and Sq-1 lung cancer cell lines were used. It has been confirmed that the two cell lines both express SUV39H2 and also express HLA-A24. As a negative control, the K562 chronic myeloid leukemia cell line, which is known not to express HLA, was used.

The results are shown in FIG. 11. A shows the result of a cytotoxic activity assay for peptide-pulsed T2-A24 cells; there was no cytotoxic activity toward non-peptide-pulsed and HIV peptide-pulsed T2-A24, but strong cytotoxic activity was shown toward RF8 peptide-pulsed T2-A24. Furthermore, B shows the result of a cytotoxic activity assay toward various types of cancer cell lines; strong cytotoxic activity was also shown toward all of SW480, LHK2, and Sq-1 cell lines. On the other hand, no cytotoxic activity was shown toward the K562 negative control. This result shows that RF8 peptide is naturally presented on HLA-A24 of SUV39H2-expressing cells, and the CTL simultaneously induced exhibits an anti-tumor effect toward cancer cells.

INDUSTRIAL APPLICABILITY

The peptide of the present invention is a peptide that is specifically presented as an antigen on a tumor, and is very useful as a target of therapy tumor-specific such as molecularly targeted therapy, immunotherapy, nucleic acid therapy, etc. In particular, these peptides are identified as peptides that are actually antigens presented as a complex with HLA-A24 on a cancer cell surface, and therefore can be particularly suitably used in immunotherapy.

The invention claimed is:

1. A vaccine composition comprising (a) or (b) below as an active ingredient, an adjuvant, and a pharmaceutically acceptable carrier:
(a) an expression vector comprising a polynucleotide encoding a tumor antigen peptide that comprises SEQ ID NO: 1, SEQ ID NO: 2, SEQ ID NO: 3, SEQ ID NO: 4 or SEQ ID NO: 5, or
(b) an expression vector comprising a polynucleotide encoding SUV39H2, ZNF724P, SNRNP40, DYRK4, or SNRNP40.

2. A vaccine composition comprising any one of (a)-(c) below as an active ingredient, an adjuvant, and a pharmaceutically acceptable carrier:
(a) a tumor antigen peptide according to any one of SEQ ID NOs: 1-5, or
(b) the polynucleotide encoding the tumor antigen peptide of (a) or an expression vector containing said polynucleotide, or
(c) an expression vector containing a polynucleotide encoding a protein selected from the group consisting of SUV39H2, ZNF724P, SNRNP40, and DYRK4.

3. An HLA multimer comprising an HLA and a tumor antigen peptide according to any one of SEQ ID NOs: 1-5, wherein the HLA multimer is not a monomer.

4. A diagnostic agent comprising the HLA multimer according to claim 3.

5. An agent for inducing a cytotoxic T cell, the agent comprising a protein encoded by a gene selected from the group consisting of SUV39H2, ZNF724P, SNRNP40, and DYRK4, or a polynucleotide encoding said protein, an adjuvant, and a pharmaceutically acceptable carrier.

6. An agent for inducing a cytotoxic T cell, the agent comprising an antigen-presenting cell presenting a tumor antigen peptide according to any one of SEQ ID NOS: 1-5 as an antigen, an adjuvant, and a pharmaceutically acceptable carrier.

7. A pharmaceutical composition comprising a protein encoded by a gene selected from the group consisting of SUV39H2, ZNF724P, SNRNP40, and DYRK4, or a polynucleotide encoding said protein, an adjuvant, and a pharmaceutically acceptable carrier.

8. An agent for inducing a cytotoxic T cell, the agent comprising an expression vector comprising a polynucleotide encoding a tumor antigen peptide that comprises SEQ ID NO: 1, SEQ ID NO: 2, SEQ ID NO: 3, SEQ ID NO: 4 or SEQ ID NO: 5, or an expression vector comprising a polynucleotide encoding SUV39H2, ZNF724P, SNRNP40, DYRK4, or SNRNP40; and an adjuvant, and a pharmaceutically acceptable carrier.

9. An agent for inducing a cytotoxic T cell, the agent comprising an antigen-presenting cell comprising an expression vector containing a polynucleotide encoding the tumor antigen peptide according to any one of SEQ ID NOs: 1-5, or an antigen-presenting cell comprising an expression vector containing a polynucleotide encoding a protein selected from the group consisting of SUV39H2, ZNF724P, SNRNP40, and DYRK4, and a pharmaceutically acceptable carrier.

10. A pharmaceutical composition comprising an expression vector comprising a polynucleotide encoding a tumor antigen peptide that comprises SEQ ID NO: 1, SEQ ID NO: 2, SEQ ID NO: 3, SEQ ID NO: 4 or SEQ ID NO: 5, or an expression vector comprising a polynucleotide encoding SUV39H2, ZNF724P, SNRNP40, DYRK4, or SNRNP4; and an adjuvant, and a pharmaceutically acceptable carrier.

\* \* \* \* \*